US008610967B2

(12) United States Patent
Ikari et al.

(10) Patent No.: US 8,610,967 B2
(45) Date of Patent: Dec. 17, 2013

(54) ILLUMINATION APPARATUS AND IMAGE READING APPARATUS INCLUDING THE SAME

(75) Inventors: Seiji Ikari, Yokohama (JP); Hiroshi Fukuta, Yokohama (JP); Takeshi Morino, Yokohama (JP); Yoshinori Honguh, Yokohama (JP); Masataka Shiratsuchi, Kawasaki (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 13/465,113

(22) Filed: May 7, 2012

(65) Prior Publication Data

US 2012/0218611 A1    Aug. 30, 2012

Related U.S. Application Data

(63) Continuation of application No. PCT/JP2011/052094, filed on Feb. 2, 2011.

(30) Foreign Application Priority Data

Feb. 5, 2010    (JP) ................................ 2010-024525
Sep. 7, 2010    (JP) ................................ 2010-200042

(51) Int. Cl.
     *H04N 1/04*      (2006.01)
(52) U.S. Cl.
     USPC ........................... 358/474; 358/471; 358/475
(58) Field of Classification Search
     USPC ......... 358/400, 471, 474, 482, 483, 494, 496, 358/475
See application file for complete search history.

(56) References Cited

U.S. PATENT DOCUMENTS

| 4,814,630 | A | 3/1989 | Lim |
| 5,019,897 | A | 5/1991 | Shirata et al. |
| 7,619,787 | B2* | 11/2009 | Mikajiri et al. ............... 358/475 |
| 7,852,523 | B2* | 12/2010 | Cho et al. ...................... 358/484 |

FOREIGN PATENT DOCUMENTS

| JP | 56-169472 | 12/1981 |
| JP | 60-230621 | 11/1985 |
| JP | 01-503751 | 12/1989 |
| JP | 02-000750 | 1/1990 |
| JP | 02-19064 | 1/1990 |
| JP | 03-116056 | 5/1991 |
| JP | 06-22087 | 1/1994 |
| JP | 2001-268320 | 9/2001 |
| JP | 2001-330734 | 11/2001 |

(Continued)

OTHER PUBLICATIONS

Japanese Office Action dated May 8, 2012.

(Continued)

*Primary Examiner* — Thomas D Lee
(74) *Attorney, Agent, or Firm* — Pillsbury Winthrop Shaw Pittman, LLP

(57) ABSTRACT

According to one embodiment, illumination apparatus including, first light source module which includes light-emitting module that emits light, light-emitting module having line shape, and first reflection member which includes first reflection surface that reflects light emitted from light-emitting module of first light source module for predetermined range, wherein first reflection surface has cross section that has zigzag line shape including plurality of line segments running along standard oval, which has major axis that forms predetermined angle with direction perpendicular to predetermined range, in direction perpendicular to longitudinal direction of light-emitting module of first light source module.

19 Claims, 12 Drawing Sheets

(56) References Cited

FOREIGN PATENT DOCUMENTS

| | | |
|---|---|---|
| JP | 2003-344958 | 12/2003 |
| JP | 2005-277779 | 10/2005 |
| JP | 2007-071763 | 3/2007 |
| JP | 2007-193287 | 8/2007 |
| JP | 2010-110938 | 5/2010 |

OTHER PUBLICATIONS

International Search Report for PCT/JP2011/052094, Mar. 8, 2011.

* cited by examiner

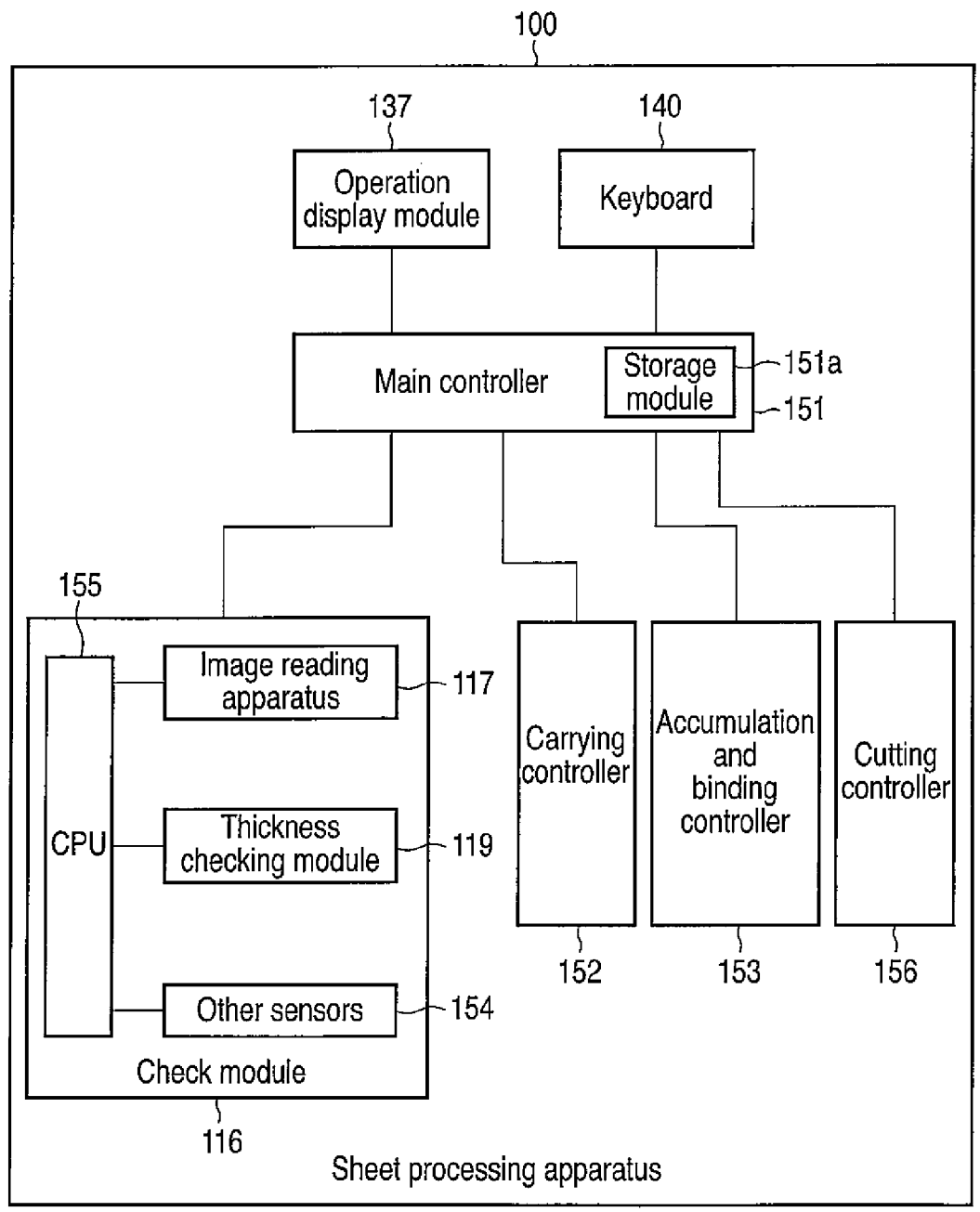
F I G. 3

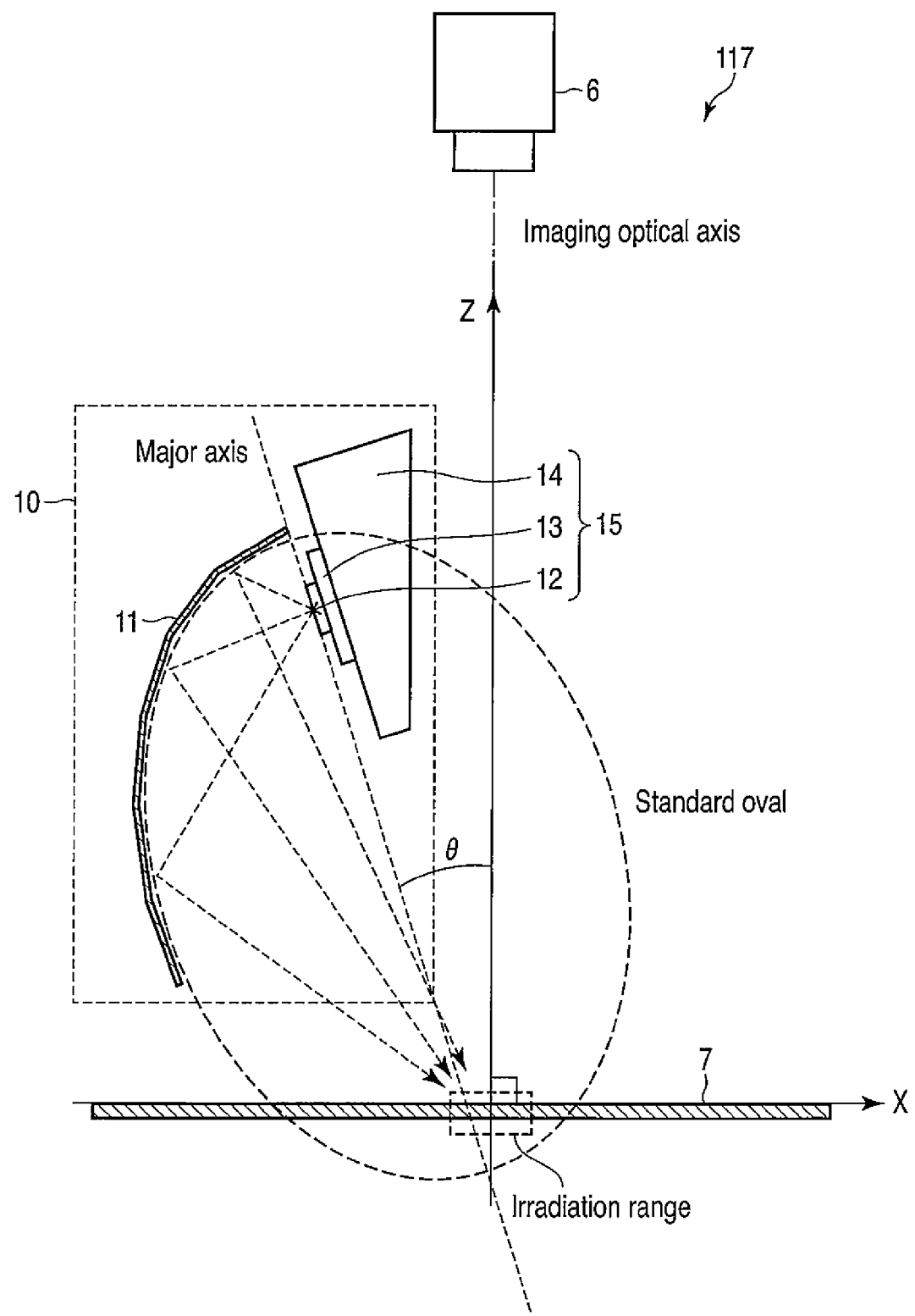
F I G. 4

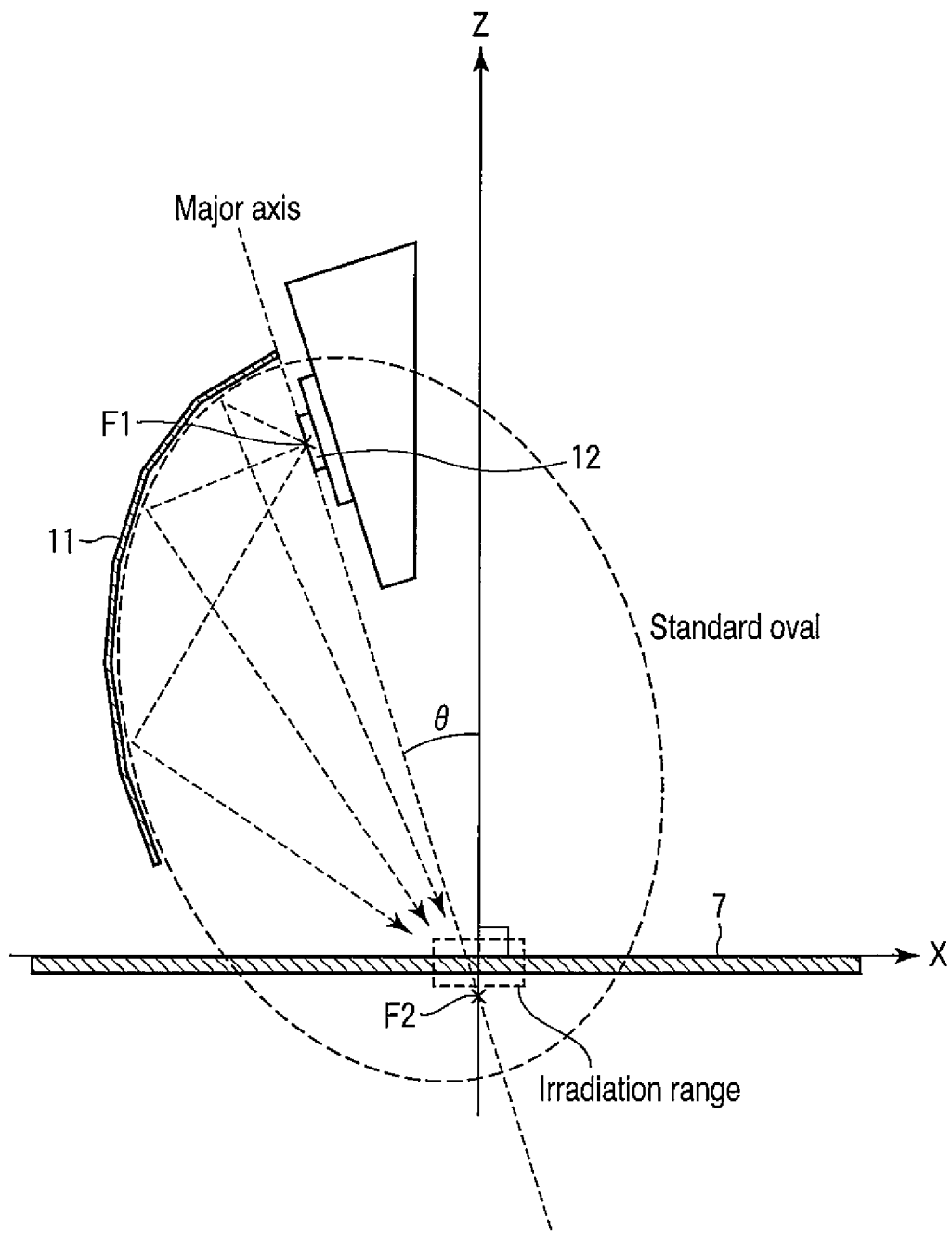
F I G. 7

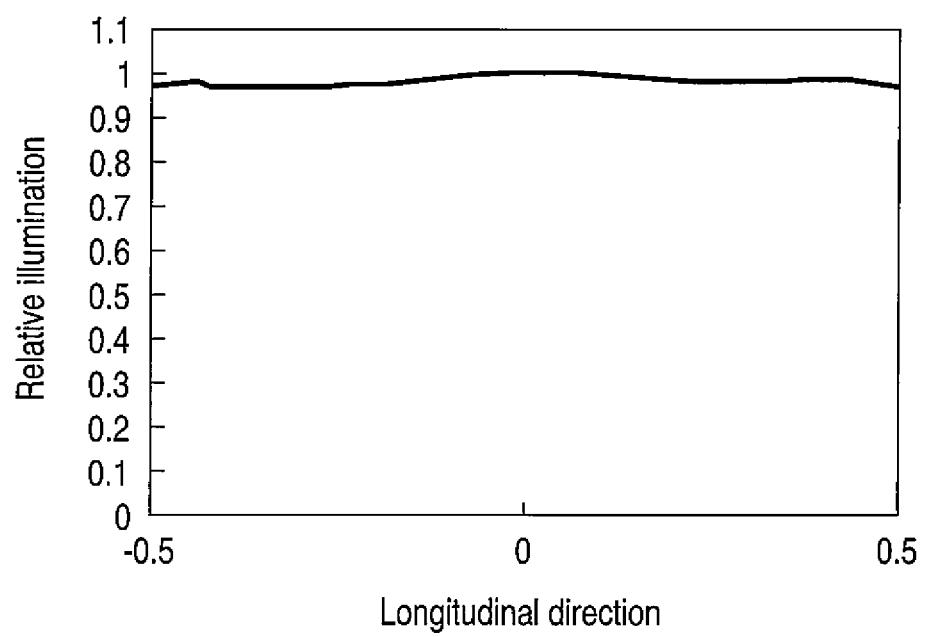
F I G. 12

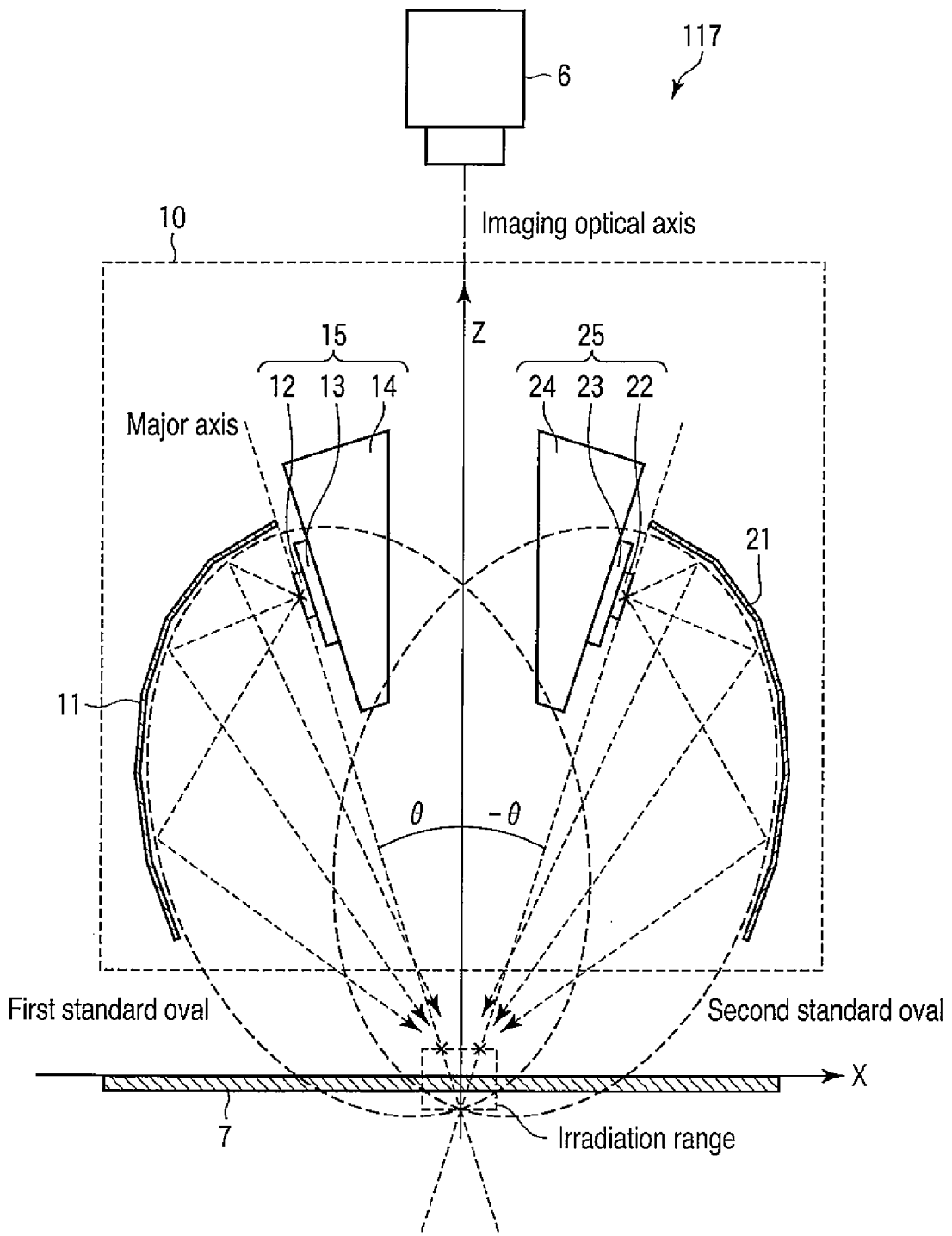
F I G. 13

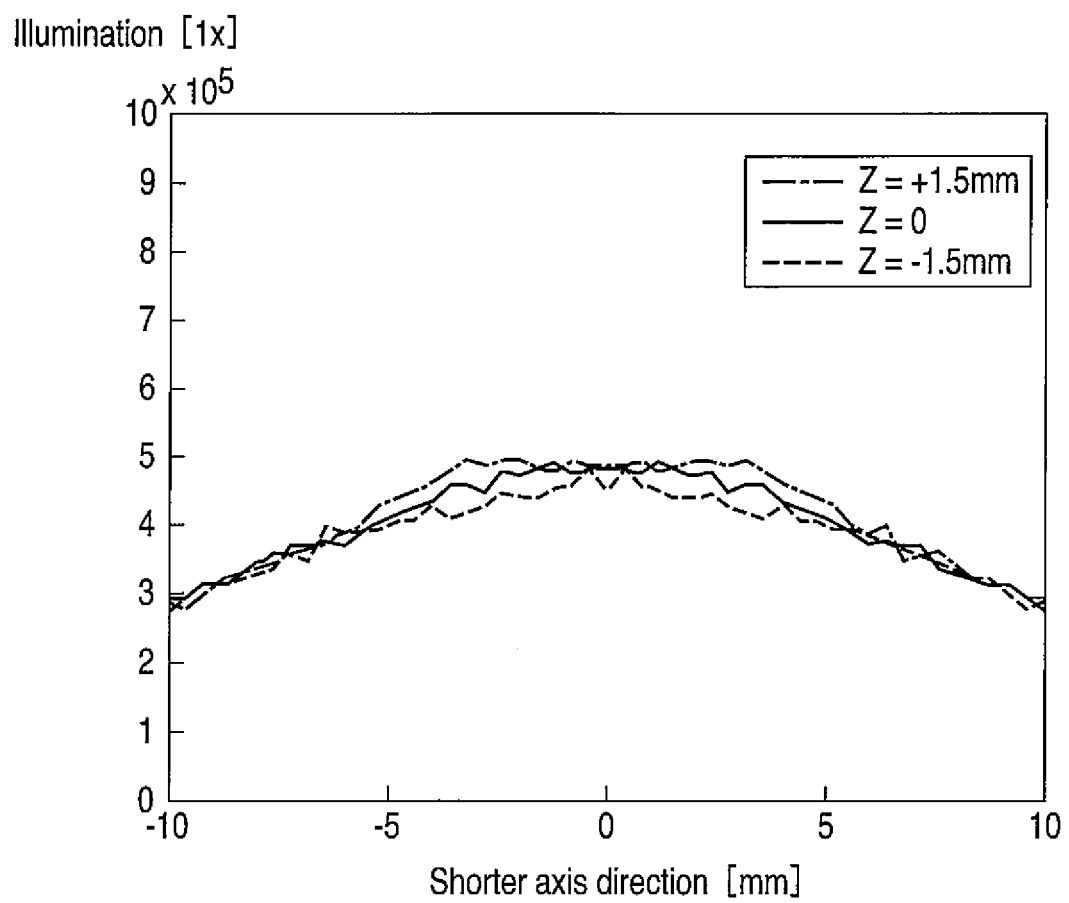
F I G. 17

ILLUMINATION APPARATUS AND IMAGE READING APPARATUS INCLUDING THE SAME

CROSS REFERENCE TO RELATED APPLICATIONS

This application is a Continuation Application of PCT Application No. PCT/JP2011/052094, filed Feb. 2, 2011 and based upon and claiming the benefit of priority from prior Japanese Patent Applications No. 2010-024525, filed Feb. 5, 2010; and No. 2010-200042, filed Sep. 7, 2010, the entire contents of all of which are incorporated herein by reference.

FIELD

Embodiments described herein relate generally to an illumination apparatus, and an image reading apparatus including the illumination apparatus.

BACKGROUND

In prior art, sheet processing apparatuses which checks various sheets such as paper money have been put to practical use. The sheet processing apparatuses have an image reading apparatus which reads images of sheets. The sheet processing apparatuses takes in sheets which are put into an inlet one by one, and carries the sheets to the image reading apparatus.

The image reading apparatus includes an illumination module (illumination apparatus) and a line image sensor. The image reading apparatus irradiates each sheet which is carried in a predetermined direction with light by the illumination apparatus. The image reading apparatus reads transmission light or reflection light of the light applied to the carried sheet by the line image sensor, and obtains an image of the sheet.

The illumination apparatus irradiates a surface of each sheet as a test subject with light. In this case, the illumination apparatus desirably has an illumination distribution which is uniform in the longitudinal direction of the line image sensor. When high-speed and accurate processing is performed, the illumination module is required to have high and uniform illumination to reduce the load of image processing and signal processing.

The illumination module has a light source such as a halogen light source and a fluorescent light, and a light guide (light-guiding member) using light fiber. In addition, in recent years, illumination modules which have a light source using light emitting diodes (hereinafter simply referred to as LEDs) are having been put to practical use. The illumination modules have LEDs which are arranged in a straight line or rows and columns.

However, in a light source device in which light-emitting devices such as LEDs are arranged, the illumination distribution on a test subject is a distribution obtained by superposing illumination distributions of respective light-emitting devices in a three-dimensional manner. Therefore, in the case of using light-emitting devices which have a high-directional light distribution and have a structure of uniting an LED with a lens, the illumination distribution of each light-emitting device has a narrow range and a bell shape, and the illumination distribution obtained by superposing the illumination distributions of the light-emitting devices have a wave shape, and has a problem of generating non-uniform illumination. In addition, since the light-emitting devices have high directivity, unevenness in the total illumination distribution is easily caused by difference in position and angle between the individual light-emitting devices.

On the other hand, in the case of using light-emitting devices which have low directivity and have a structure in which an LED is not united with a lens, an area to which one light-emitting device applies light is increased. Therefore, although a part around the center of the test subject is irradiated with light beams which come from both directions as viewed from the center of the test subject, a part around the edge of the test subject is irradiated with only light which comes from one direction in which the LED exists as viewed from the edge. This causes the problem of unevenness in illumination, that is, the part around the center of the test subject has high illumination distribution, and the illumination gradually decreases toward the edge.

As a method of preventing unevenness in illumination, there is a method of reducing a light-emitting quantity of light-emitting devices around the center of the test subject by flowing a small quantity of current through them, increasing a light-emitting quantity of light-emitting devices around the edge by flowing a large quantity of current through them, and thereby balancing the illumination. However, this method cannot sufficiently exhibit the brightness performance of the light-emitting devices.

Although there is also a method of increasing the light-emitting quantity around the edge by increasing the density of the light-emitting devices around the edge, and thereby preventing decrease in illumination, it is physically impossible to increase the density of the light-emitting devices more than the size of each light-emitting device, and thus increase in the light-emitting quantity is limited.

In addition, there is an illumination apparatus including a reflection member which has an oval-arc-shaped cross section in the sheet carrying direction, to collect light emitted from the light source into a reading range of the line image sensor. However, in the case of using a reflection member having an oval-arc-shaped cross section, the illumination distribution has a pointed peak.

When the illumination distribution has a pointed peak, the range in which the illumination apparatus has uniform illumination is narrowed. Therefore, there is the problem that it is difficult to install the line image sensor and the illumination apparatus such that the reading range of the line image sensor agrees with the peak of the illumination distribution.

In addition, since the peak of the illumination distribution is pointed, the illumination distribution is not uniform in the reading range of the line image sensor. This causes the problem that uneven brightness may occur in the read image according to the sheet carrying state or the like.

BRIEF DESCRIPTION OF THE DRAWINGS

FIG. 3 is a diagram for explaining a structure example of a control system of the sheet processing apparatus according to the embodiment.

FIG. 4 is a diagram for explaining a structure example of an image reading apparatus according to the embodiment.

FIG. 7 is a diagram for explaining an example of an arranging position of the illumination apparatus according to the embodiment.

FIG. 12 is a diagram for explaining illumination distributions in the illumination apparatus according to the embodiment.

FIG. 13 is a diagram for explaining another structure example of the image reading apparatus according to the embodiment.

FIG. 17 is a diagram for explaining illumination distributions in the illumination apparatus according to the embodiment.

DETAILED DESCRIPTION

In general, according to one embodiment, an illumination apparatus according to an embodiment comprises a light source module, and a reflection member. The light source module includes a light-emitting module that emits light and has a line shape. The reflection member includes a first reflection surface that reflects the light emitted from the light-emitting module of the first light source module for a predetermined range. The reflection surface has a cross section that has a zigzag line shape including a plurality of line segments running along a standard oval, which has a major axis that forms a predetermined angle with a direction perpendicular to the predetermined range, in a direction perpendicular to a longitudinal direction of the light-emitting module of the first light source module.

The following is detailed explanation of an illumination apparatus according to an embodiment, an image reading apparatus including the illumination apparatus, and a sheet processing apparatus including the image reading apparatus, with reference to drawings.

First Embodiment

Figure 1:
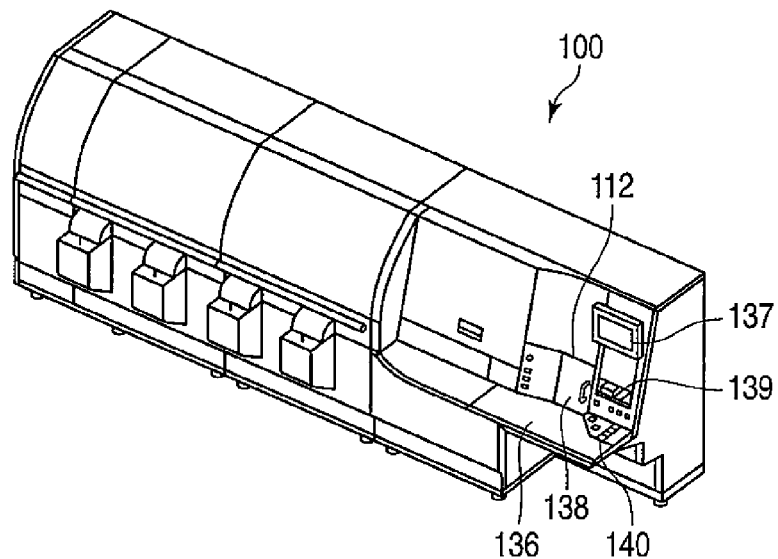
FIG. 1 is a diagram for explaining an external appearance of a sheet processing apparatus according to an embodiment.

FIG. 1 is an explanatory diagram for explaining an external appearance of a sheet processing apparatus 100 according to an embodiment.

As illustrated in FIG. 1, the sheet processing apparatus 100 comprises an inlet module 112, an operation module 136, an operation display module 137, a door 138, a takeout port 139, and a keyboard 140, which are provided on an outside part of the apparatus.

The inlet module 112 has a structure for putting, for example, sheets 7 as test subject into the apparatus. The inlet module 112 receives sheets 7 in a stacked state together. The operation module 136 receives various operation inputs performed by the operator. The operation display module 137 displays various operation guides and processing results for the operator. The operation display module 137 may be formed as a touch panel. In such a case, the sheet processing apparatus 100 detects various operation inputs, based on buttons displayed on the operation display module 137 and operations by the operator for the operation display module 137.

The door 138 is a door for opening and closing the inlet port of the inlet module 112. The takeout port 139 has a structure of taking out sheets 7 from an accumulation module in which sheets 7, which have been determined by the sheet processing apparatus 100 as not being able to be circulated again, are stacked. The keyboard 140 functions as an input module which receives various operation inputs by the operator.

Figure 2:
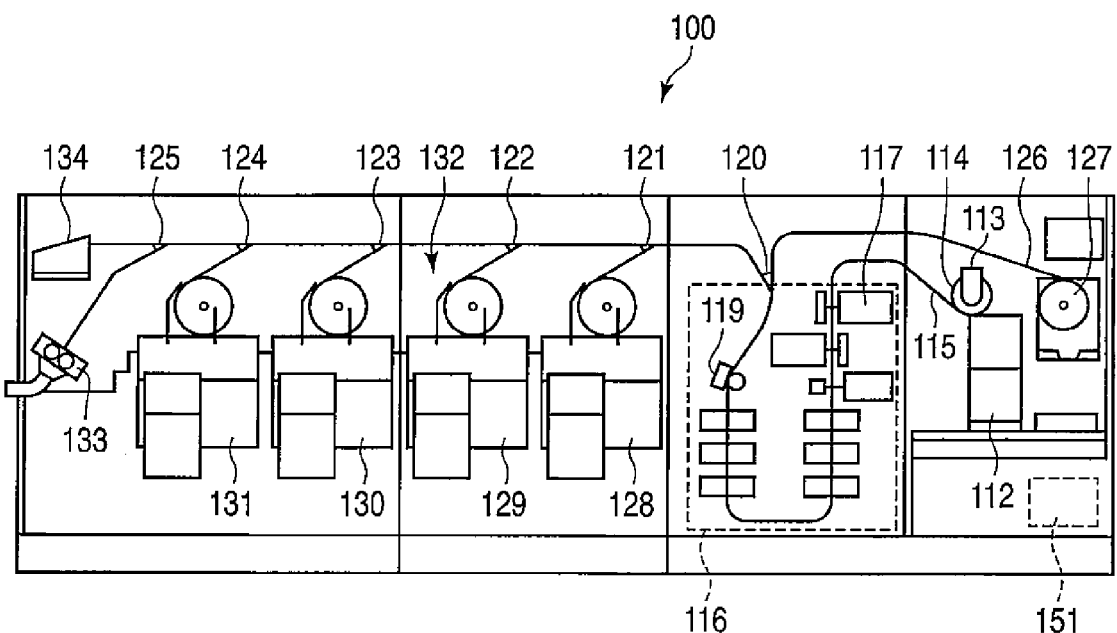
FIG. 2 is a diagram for explaining a structure example of the sheet processing apparatus according to the embodiment.

FIG. 2 is an explanatory diagram for explaining a structure example of the sheet processing apparatus 100 illustrated in FIG. 1.

The sheet processing apparatus 100 includes the inlet module 112, a takeout module 113, an adsorption roller 114, a carrying path 115, a check module 116, gates 120 to 125, a rejection carrying path 126, a rejection accumulation module 127, accumulation and binding module 128 to 131, a cutter 133, and a stacker 134. The sheet processing apparatus 100 also includes a main controller 151. The main controller 151 controls operations of the modules of the sheet processing apparatus 100 together.

The takeout module 113 is provided above the inlet module 112. The takeout module 113 includes the adsorption roller 114. The adsorption roller 114 is provided in contact with an upper accumulation end of sheets 7, which are set in the inlet module 112. Specifically, the adsorption roller 114 rotates and thereby takes each of the sheets 7 which are set in the inlet module 112 into the apparatus one by one from the upper accumulation end. The adsorption roller 114 functions to take out one sheet 7 for, for example, each one rotation. Thereby, the adsorption roller 114 takes out sheets 7 at certain pitches. The sheets 7 which are taken by the adsorption roller 114 are introduced into the carrying path 115.

The carrying path 115 is carrying means for carrying the sheets 7 to various modules in the sheet processing apparatus 100. The carrying path 115 includes a carrying belt and a driving pulley, which are not shown. The carrying path 115 operates the carrying belt by a driving motor (not shown) and the driving pulley. The carrying path 115 carries the sheets 7, which are taken by the adsorption roller 114, by the carrying belt at fixed speed. A side of the carrying path 115 which is close to the takeout module 113 is referred to as upstream side, and a side which is close to the stacker 134 is referred to as downstream side.

The check module 116 is provided on the carrying path 115 which extends from the takeout module 113. The check module 116 includes an image reading apparatus 117, and a thickness checking module 119. The check module 116 detects optical characteristic information, a mechanical characteristic, and magnetic characteristic information of each sheet 7. Thereby, the sheet processing apparatus 100 checks the type, stains and damage, the side, and the legal/illegal state of each sheet 7.

The image reading apparatus 117 includes a reading module which has a plurality of imaging devices such as charge coupled devices (CCD), and an illumination apparatus. The reading module functions as, for example, a line image sensor. In such a case, the reading module has a plurality of imaging devices which are arranged in a direction perpendicular to the carrying direction of the sheets 7.

The image reading apparatus 117 reads an image of each sheet 7 which is carried through the carrying path 115. The image reading apparatus 117 may have a structure of being provided on one side of the carrying path 115, or a structure of being provided to face both sides of the carrying path 115. When the image reading apparatus 117 is provided to face the both sides of the carrying path 115, the image reading apparatus 117 can reads images of both sides of each sheet 7 which is carried through the carrying path 115.

The image reading apparatus 117 temporarily stores the read image in a memory (not shown) in the check module 116. The sheet processing apparatus 100 can display the image stored in the memory on the operation display module 137 in response to an operation input.

The thickness check module 119 checks the thickness of each sheet 7 carried through the carrying path 115. For example, when the detected thickness exceeds a predetermined value, the sheet processing apparatus 100 detects that two sheets 7 are taken together and overlap each other.

In addition, the check module 116 may further include, for example, a magnetic sensor which detects magnetism from each sheet 7 carried through the carrying path 115.

The main controller 151 determines the type, the legal/illegal state, and the fit/unfit state of each sheet 7, and whether each sheet 7 is to be rejected or not, based on detection results by the image reading apparatus 117 and the thickness checking module 119.

The main controller 151 determines whether each sheet 7 is legal or illegal, based on detection results of the modules. The main controller 151 determines each sheet 7 which fits preset parameters as a legal sheet, and determines each sheet 7 which does not fit the preset parameters as an illegal sheet.

In addition, the main controller 151 determines the type of each sheet 7, based on detection results of the modules and preset parameters.

The main controller 151 also determines whether each sheet 7 is suitable for recirculation or not (whether each sheet is a fit sheet or an unfit sheet), based on detection results of the modules and preset parameters. Specifically, the main controller 151 determines each sheet 7 which fits preset parameters as a fit sheet, and each sheet 7 which does not fit preset parameters as an unfit sheet.

The sheet processing apparatus 100 carries sheets 7 which are determined as fit sheets to the accumulation and binding modules 128 to 131. The sheet processing apparatus 100 carries sheets 7 which are determined as unfit sheets to the cutter 133. The cutter 133 cuts the carried unfit sheets. The sheet processing apparatus 100 may carry the unfit sheets to the stacker 134 and accumulate the sheets in the stacker 134. The stacker 134 seals the accumulated unfit sheets each time when, for example, the number of the accumulated unfit sheets reaches 100.

In addition, the main controller 151 determines two sheets 7 taken together, sheets 7 which include a folded or broken part, sheets 7, the type of which is unidentified, and illegal sheets, as rejected sheets. The main controller 151 controls the modules to carry sheets 7 which are determined as rejected sheets to the rejection accumulation module 127.

Gates 120 to 125 are arranged in order in a part of the carrying path 115 downstream the check module 116. Each of the gates 120 to 125 is controlled by the main controller 151. The main controller 151 controls operation of each of the gates 120 to 125, based on a result of checking by the check module 116. Thereby, the main controller 151 performs control to carry each sheet 7 which is carried through the carrying path 115 to a predetermined processing module.

The gate 120 which is provided directly after the check module 116 branches the carrying path 115 to a rejection carrying path 126. Specifically, the main controller 151 controls the gate 120 to carry sheet 7 which is determined as a rejected sheet to the rejection carrying path 126.

An end part of the rejection carrying path 126 is provided with the rejection accumulation module (rejection module) 127. The rejection accumulation module 127 accumulates rejected sheets which are in an attitude of being taking out of the takeout module 113. The sheets 7 which are accumulated in the rejection accumulation module 127 can be taken out of the takeout port 139.

Parts which are branched from the carrying path 115 by the gates 121 to 124 are provided with the accumulation and binding modules 128 to 131 (hereinafter referred to as "accumulation and binding module 132" together), respectively. Sheets 7 which are determined as being recirculatable are accumulated in the accumulation and binding module 132, in groups which are divided according to the type and the sides. The accumulation and binding module 132 binds the accumulated sheets 7 for each predetermined number of sheets, and stores the bound sheets. In addition, the sheet processing apparatus 100 accumulates and binds a plurality of bundles of sheets 7, each of which includes the predetermined number of sheets, by a bundle module (not shown).

A part which is branched from the carrying path 115 by the gate 125 is provided with the cutter 133 and the stacker 134. The cutter 133 cuts and stores the carried sheets 7. The stacker 134 accumulates the carried sheets 7. The main controller 151 controls the gates 121 to 124 to carry each sheet 7 which is determined as an unfit sheet to the gate 125.

When an unfit sheet cutting mode is selected by operation inputted from the outside, the main controller 151 controls the gate 125 to carry unfit sheets 7 to the cutter 133. When the unfit sheet cutting mode is not selected, the main controller 151 controls the gate 125 to carry unfit sheets 7 to the stacker 134.

The main controller 151 successively stores the number of sheets 7 which are accumulated in the accumulation and binding module 132, and the number and identification information of sheets 7 which are cut by the cutter 133.

FIG. 3 is an explanatory diagram for explaining a structure example of a control system of the sheet processing apparatus 100 illustrated in FIG. 1 and FIG. 2.

The sheet processing apparatus 100 comprises the main controller 151, the check module 116, a carrying controller 152, an accumulation and binding controller 153, a cutting controller 156, the operation display module 137, and the keyboard 140.

The main controller 151 performs the whole control of the sheet processing apparatus 100. The main controller 151 controls the carrying controller 152 and the accumulation and binding controller 153, based on operations inputted by the operation display module 137 and checking results obtained by the check module 116.

For example, the operator inputs the type, the number of sheets, the fit/unfit determination level, the name of the supplier, and the processing method of sheets 7 to be processed, by the operation display module 137 or the keyboard 140.

The check module 116 includes the image reading apparatus 117, the thickness checking module 119, and other sensors 154, and a CPU 155.

The image reading apparatus 117 reads an image of each sheet 7 which is carried through the carrying path 115. The image reading apparatus 117 lights the illumination apparatus based on control by the main controller 151, and irradiates each sheet 7 with light. The image reading apparatus 117 receives reflection light or transmission light from each sheet 7, forms an image of the received light on the imaging device, and obtains an electric signal (image).

The main controller 151 stores an image (reference image) which serves as a standard of sheets 7 in the storage module 151a in advance. The main controller 151 performs various determinations, by comparing the image obtained from each sheet 7 with the reference image stored in the storage module 151a.

The thickness checking module 119 checks the thickness of each sheet 7 which is carried through the carrying path 115. The other sensors 154 include, for example, a magnetic sensor and/or an ultraviolet image obtaining module. The magnetic sensor detects magnetism from each sheet 7. The ultraviolet image obtaining module irradiates each sheet 7 carried through the carrying path 115 with ultraviolet light, and detects excited light emitted from fluorescent material applied onto the sheet 7.

The CPU 155 unites checking results obtained by the image reading apparatus 117, the thickness checking module 119, and the other sensors 154. The CPU 155 may have a structure of determining the type, the fit/unfit state, the side, and the legal/illegal state of each sheet 7 carried through the carrying path 115, based on the checking results obtained by the modules.

The carrying controller 152 controls the takeout module 113, the carrying path 115, the rejection carrying path 126, and the gates 120 to 125, based on control by the main controller 151. Thereby, the carrying controller 152 controls taking and carrying of the sheets 7. The carrying controller 152 also performs sorting processing of sorting the determined sheets 7 according to the type. Specifically, the carrying controller 152 functions as a sorting processing module.

The accumulation and binding controller 153 controls the rejection accumulation module 127 and the accumulation and binding modules 128 to 131, based on control by the main controller 151. Thereby, the accumulation and binding controller 153 controls accumulation and binding of sheets 7.

The cutting controller 156 controls operation of the cutter 133, based on control by the main controller 151. Thereby, the cutter 133 cuts the sheets 7 which are carried to the cutter 133.

FIG. 4 is an explanatory diagram for explaining a structure example of the image reading apparatus 117 illustrated in FIG. 2 and FIG. 3. The image reading apparatus 117 is installed in, for example, the vicinity of the carrying path 115 of the sheet processing apparatus 100. In this example, suppose that the sheets 7 are carried in a direction of an arrow a (carrying direction) by the carrying path 115. The carrying direction a is parallel with an x axis direction illustrated in FIG. 4.

The image reading apparatus 117 includes a reading module 6 and the illumination apparatus 10.

As described above, the reading module 6 detects optical characteristic information (optical image) of each sheet 7. For example, the reading module 6 has an imaging optical axis of a direction (z axis direction) perpendicular to a predetermined range on the carried sheet 7, as illustrated in FIG. 4. The reading module 6 receives transmission light or reflection light of the light applied from the illumination apparatus 10 to the sheet 7, and obtains an image of the sheet 7.

The reading module 6 includes imaging devices such as CCDs, and an imaging lens. The imaging devices convert light imaged by the imaging lens into an electric signal (image). The reading module 6 includes a plurality of imaging devices which are arranged in a direction perpendicular to the carrying direction a of the sheets 7. Specifically, the reading module 6 includes a line image sensor.

The reading module 6 receives light from a predetermined range (reading range) which has the same size as, or a size narrower than, a predetermined range (irradiation range) to which light is applied by the illumination apparatus 10, and obtains an image. The reading module 6 successively obtains images from each sheet 7 carried by the carrying path 115, and thereby obtains a whole image of the sheet 7.

The reading module 6 may have a structure including a plurality of line image sensors, a dichroic prism, and color filters. The reading module 6 divides light by the dichroic prism, and filters the divided light beams by the color filters. Thereby, the reading module 6 can form images of light beams of a plurality of different wavelengths on different line image sensors.

The imaging lens of the reading module 6 forms an image of the surface of the sheet 7 on the line image sensor. The imaging optical axis of the reading module 6 may have any structure, as long as the optical axis satisfies such an image formation relation and relation between the imaging optical axis of the reading module 6 and the illumination apparatus 10 described later. For example, the imaging optical axis of the reading module 6 may be bent by using a mirror or a light-guiding member.

The illumination apparatus 10 applies light to the predetermined range on the carried sheet 7 at timing based on control by the main controller 151. The illumination apparatus 10 applies light to an irradiation range (irradiated range) which is at least larger than the reading range of the reading module 6.

Although the reading module 6 and the illumination apparatus 10 of the imaging reading apparatus 117 are explained as having the structure of obtaining images based on control by the main controller 151, they are not limited to this structure. The image reading apparatus 117 may have a structure including a sensor which detects the position of each sheet 7 carried by the carrying path 115, and a controller which automatically controls operations of the reading module 6 and light-emitting devices 12 based on a detection result of the sensor.

The illumination apparatus 10 includes a light source module 15 and a reflection member 11. FIG. 4 illustrates a cross-section of the reflection member 11 in the carrying direction of the sheet 7. The light source module 15 includes a light-emitting device 12, a mounting board 13, and a heat radiation member 14.

The light-emitting element 12 is a light-emitting device which emits light. The light source module 15 includes LEDs which serve as a plurality of light-emitting devices 12 and are arranged in a line in a direction perpendicular to the carrying direction of the sheet 7. Specifically, the light source module 15 includes LEDs which serve as a plurality of light-emitting devices 12 and are arranged in a line in parallel with a scanning direction of the reading module 6. In other words, the light source module 15 includes a light-emitting module which is formed in a line and emits light.

Although the present embodiment shows an example of using LEDs as light-emitting devices 12, the embodiment is not limited to this structure. The light-emitting device may be a line-shaped halogen light source, or a fluorescent light. When LEDs are used as light-emitting devices 12, the light-emitting module includes a plurality of LEDs which are arranged in a line.

The mounting board 13 is a board on which LEDs serving as the light-emitting devices 12 is provided. The mounting board 13 is formed of, for example, aluminum, copper, or another material having high heat radiation property. An electric circuit to light the light-emitting devices 12 is mounted to the mounting board 13. The heat radiation member 14 is a member to radiate heat of the mounting board 13.

Figure 5:
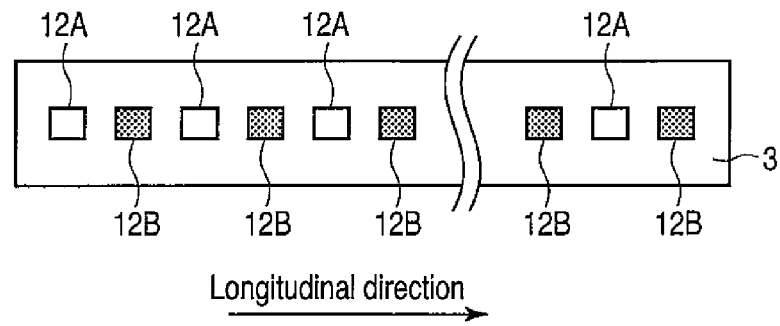
FIG. 5 is a diagram for explaining a structure example of a light source module according to the embodiment.

For example, as illustrated in FIG. 5, the light source module 15 has a structure in which light-emitting devices 12A, a center wavelength of which is a first wavelength, and light-emitting devices 12B, a center wavelength of which is a second wavelength, are alternately arranged in a line. In this case, in the irradiation range, light beams which are emitted from the light-emitting devices 12A and the light-emitting devices 12B are mixed while they are reflected by the reflection member 11 and converge in the irradiation range. Specifically, the irradiation range is irradiated with light obtained by mixing light of the first wavelength with light of the second wavelength. This structure enables the illumination apparatus 10 to suppress unevenness of wavelengths of the irradiated light. The light source module 15 may have a structure in which light-emitting devices having the same center wavelength are arranged in a line.

Figure 6:
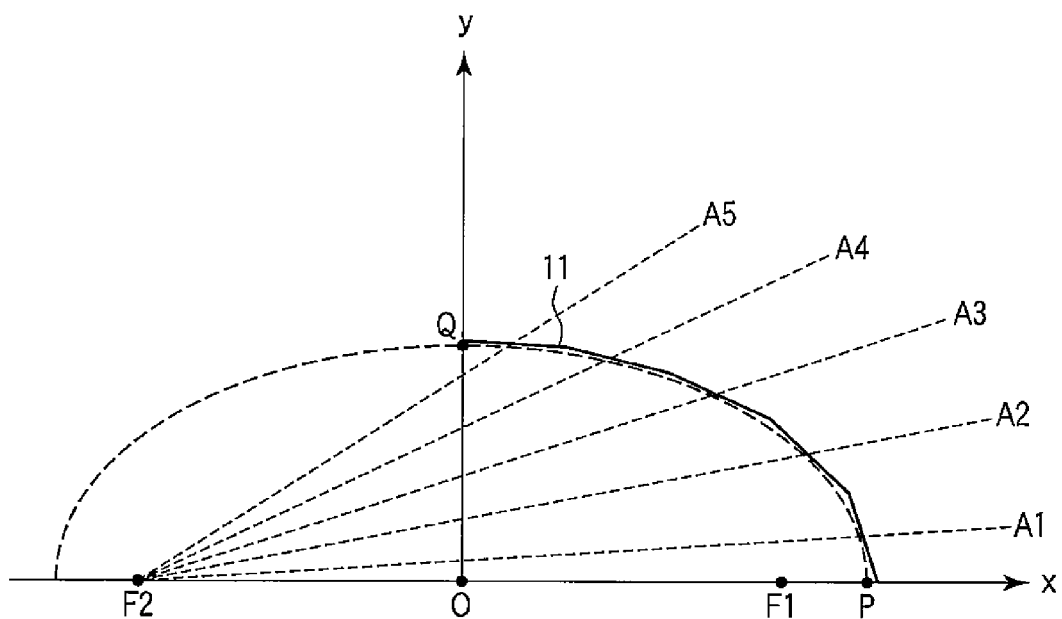
FIG. 6 is a diagram for explaining a structure example of a reflection member according to the embodiment.

The reflection member 11 has a mirror (reflection surface) which entirely reflects light. As illustrated in FIG. 6, the mirror of the reflection member 11 is formed in a zigzag line shape along an oval (standard oval) which has a straight line that has an angle θ with the imaging optical axis of the reading module 6 as the major axis. Specifically, the mirror of the reflection member 11 has a plurality of straight-line parts which are inscribed or circumscribed on the arc of the standard oval. In addition, the mirror of the reflection member 11 may have a shape in which joints of the zigzag line of the mirror exist on or in the vicinity of the standard oval.

The shape of the cross section of the mirror of the reflection member 11 is determined by, for example, the following method.

First, the standard oval is illustrated by a broken line in FIG. 6. When the rectangular coordinates are set on the assumption that the center of the standard oval is the origin O, the major axis direction is an x axis, and the minor axis direction is a y axis, a focus F1 and a focus F2 are plotted on the x axis, as illustrated in FIG. 6.

In addition, suppose that an intersection point between the standard oval and the positive part of the x axis is P, and an intersection point between the standard oval and the positive part of the y axis is Q. The mirror of the reflection member 11 is formed along an oval arc of the standard oval in the first quadrant.

The oval arc of the standard oval in the first quadrant is divided at equal angles as viewed from the focus F2. For example, the oval arc is divided by long dashed short dashed lines which are arranged at equal angles in FIG. 6. The angle between the x axis and the assistant line (A1) which is closest to the x axis is half the angle between two adjacent assistant lines. The angle which is formed between a straight line including the point F2 and the point Q and the assistant line (A5) which is closest to the y axis is half the angle between two adjacent assistant lines.

Specifically, the assistant lines A1 to An satisfy the following expressions.

$$\angle A1F2A2 = \angle A2F2A3 = \ldots = \angle An-1F2An = \theta \quad \text{[Expression 1]}$$

$$\angle PF2A1 = \angle QF2An = \frac{\theta}{2} \quad \text{[Expression 2]}$$

The symbol θ in the expressions 1 and 2 is any angle determined by the number of lines of the mirror. The symbol n in the expressions 1 and 2 denotes the number of lines in the cross section of the mirror of the reflection member 11.

Tangents of the oval arc, which have respective intersection points between the oval arc and the respective assistant lines A1 to A5 as points of contact, are identified. The mirror of the reflection member 11 is formed, such that a zigzag line which is formed with intersection points between the identified tangents as joints (bent points) is a shape of the cross section of the reflection surface of the mirror of the reflection member 11. Although the example illustrated in FIG. 6 shows the mirror of the reflection member 11 on the assumption of "n=5", the mirror is not limited to this structure.

The mirror of the reflection member 11 is formed of a metal member such as aluminum. Specifically, the metal member is shaved such that the shape of the cross section thereof is the zigzag-line shape specified by the above method. In addition, the surface of the metal member is polished, and thereby a mirror surface (reflection surface) is formed. Thereby, the mirror of the reflection member 11 is formed.

In addition, the mirror of the reflection member 11 may be formed of, for example, bent sheet metal. In this case, the sheet metal is bent such that the shape of the cross section thereof is the zigzag line shape specified by the above method. In addition, the surface of the sheet metal is polished, and thereby the reflection surface being a mirror surface is formed. Thereby, the mirror of the reflection member 11 is formed.

The mirror of the reflection member 11 may be formed by a plurality of rectangular mirrors. In such a case, the mirrors are united such that the shape of the cross section of the united mirrors is the zigzag line shape specified by the above method. Thereby, the mirror of the reflection member 11 is formed.

The reflection member 11 and the light-emitting devices 12 are arranged in, for example, a position illustrated in FIG. 12. For example, the light-emitting devices 12 are arranged in a position of a focus F1 of the standard oval which serves as the standard of the reflection member 11.

In addition, the reflection member 11 is installed such that another focus F2 of the standard oval is located in the vicinity of the reading range of the reading module 6. For example, the reflection member 11 is formed based on the standard oval in which the irradiation range on the sheet 7 is located closer to the focus F1 than the focus F2. In this case, the focus F2 is located on a side opposite to the focus F1, with the carrying path 115 interposed therebetween.

Figure 8:
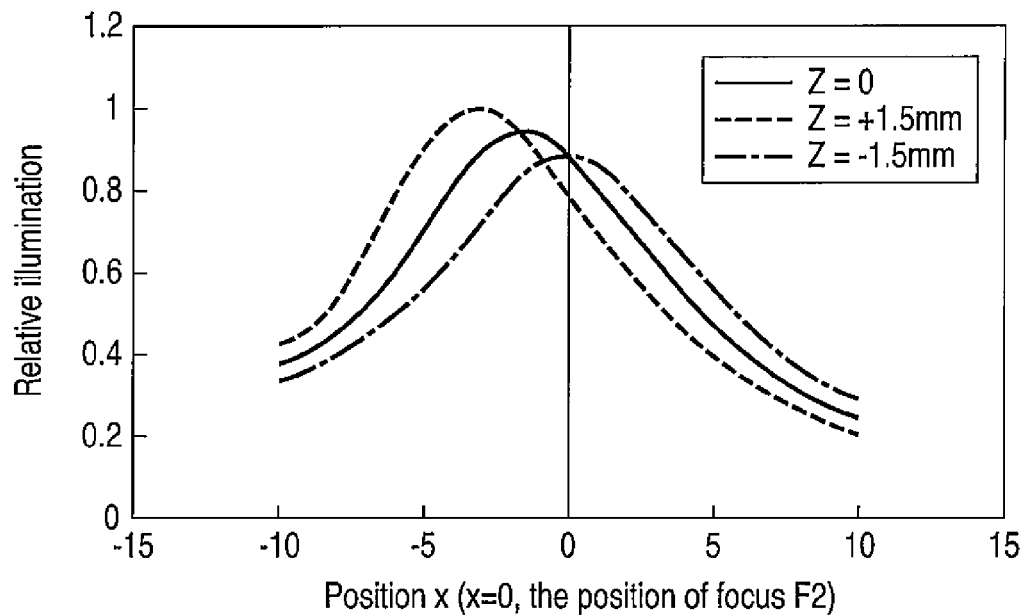
FIG. 8 is a diagram for explaining illumination in the illumination apparatus according to the embodiment.

FIG. 8 is a diagram illustrating relative illumination distributions in the illumination apparatus 10.

A solid line in the graph of FIG. 8 indicates an illumination distribution in the where the focus F2 is located in the coordinates "(x, z)=(0, 0)" in the coordinate system x and z of FIG. 7, and the irradiated area on the surface of the sheet 7 has the same height as the focus F2. A broken line in the graph indicates an illumination distribution in the case where the irradiated area is located by 1.5 mm above the focus F2 in the z axis direction. A long dashed short dashed line in the graph indicates an illumination distribution in the case where the irradiated area is located by 1.5 mm under the focus F2 in the z axis direction.

Specifically, the graph of FIG. 8 illustrates the example where the focus F2 of the standard oval is located in the coordinates "(x, z)=(0, 0)" in the coordinate system x and z illustrated in FIG. 7. The solid line in FIG. 8 indicates an illumination distribution in the case where the sheet 7 is not shifted in the direction of the imaging optical axis (z axis direction) of the reading module 6. The broken line in FIG. 8 indicates an illumination distribution in the case where the sheet 7 is shifted by +1.5 mm in the direction of the imaging optical axis (z axis direction) of the reading module 6. The long dashed short dashed line in FIG. 8 indicates an illumination distribution in the case where the sheet 7 is shifted by −1.5 mm in the direction of the imaging optical axis (z axis direction) of the reading module 6.

The illumination distributions indicated by the solid line, the broken line, and the long dashed short dashed line are standardized, with the maximum illumination of the illumination distribution obtained by optical simulation set to 1.

According to the illumination distributions illustrated in FIG. 8, the illumination in the case where the irradiation range is located by 1.5 mm above the focus F2 in the z axis direction is higher than the illumination in the case where the irradiation range is located by 1.5 mm under the focus F2 in the z axis direction. Therefore, the illumination apparatus 10 can illuminate the sheet 7 more efficiently, by installing the modules such that the irradiation range on the surface of the sheet 7 is located above the focus F2 in the z axis direction. Although an example of the illumination distribution is explained in the present embodiment, the above tendency does not depend on the number n of lines of the reflection member 11, or the length of the major axis of the standard oval.

The number n of the lines of the mirror of the reflection member 11 is determined based on the required illumination and the required illumination uniformity.

The illumination apparatus 10 desirably has high illumination in the reading range of the reading module 6, to deal with high speed carrying of the sheets 7. In addition, sheets 7 which are carried at high speed may flap, that is, shift in the direction of the imaging optical axis (z axis direction) illustrated in FIG. 7. This shift causes difference in luminance in images. To correct the difference, there are cases where electric correction is required. This may cause decrease in processing speed and/or increase in load.

Therefore, even when the sheets 7 are shifted in the direction of the imaging optical axis of the reading module 6, the illumination apparatus 10 preferably illuminates the sheets 7 with uniform illumination. For example, the image reading apparatus 117 for printed matter or cards preferably has change in illumination which falls within 10% for shift in height of the sheets 7 of about ±1.5 mm.

Figure 9:
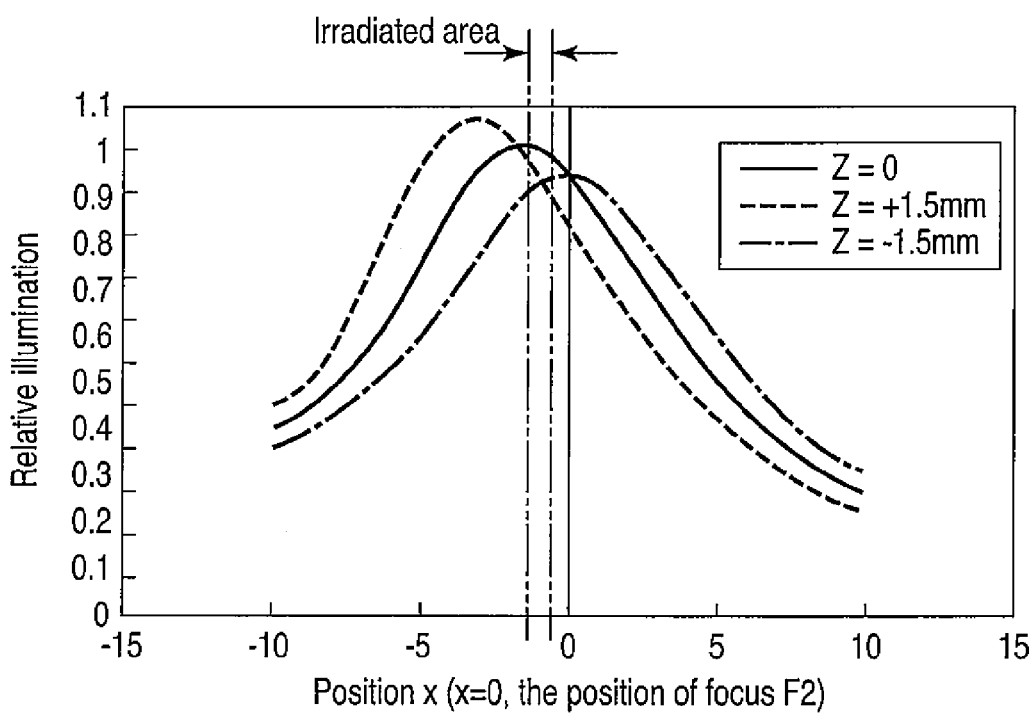
FIG. 9 is a diagram for explaining the illumination in the illumination apparatus according to the embodiment.

FIG. 9 is a diagram illustrating relative illumination distributions in the illumination apparatus 10.

A solid line in FIG. 9 indicates an illumination distribution in the case where the sheet 7 is not shifted in the direction of the imaging optical axis (z axis direction) of the reading module 6. A broken line in FIG. 9 indicates an illumination distribution in the case where the sheet 7 is shifted by +1.5 mm in the direction of the imaging optical axis (z axis direction) of the reading module 6. A long dashed short dashed line in FIG. 9 indicates an illumination distribution in the case where the sheet 7 is shifted by −1.5 mm in the direction of the imaging optical axis (z axis direction) of the reading module 6.

The illumination distributions illustrated in FIG. 9 are standardized, based on the illumination in the irradiation range in the standard position (z=0). FIG. 9 shows that difference among the illumination indicated by the solid line, the illumination indicated by the dotted line, and the illumination indicated by the long dashed short dashed line is less than 10% in the irradiation range illustrated in FIG. 9.

For example, simulation is performed with various shift quantities of the sheets 7 in the z axis direction and various numbers of lines of the reflection member 11, and thereby it is possible to specify the suitable number n of lines of the mirror of the reflection member 11.

Figure 10:
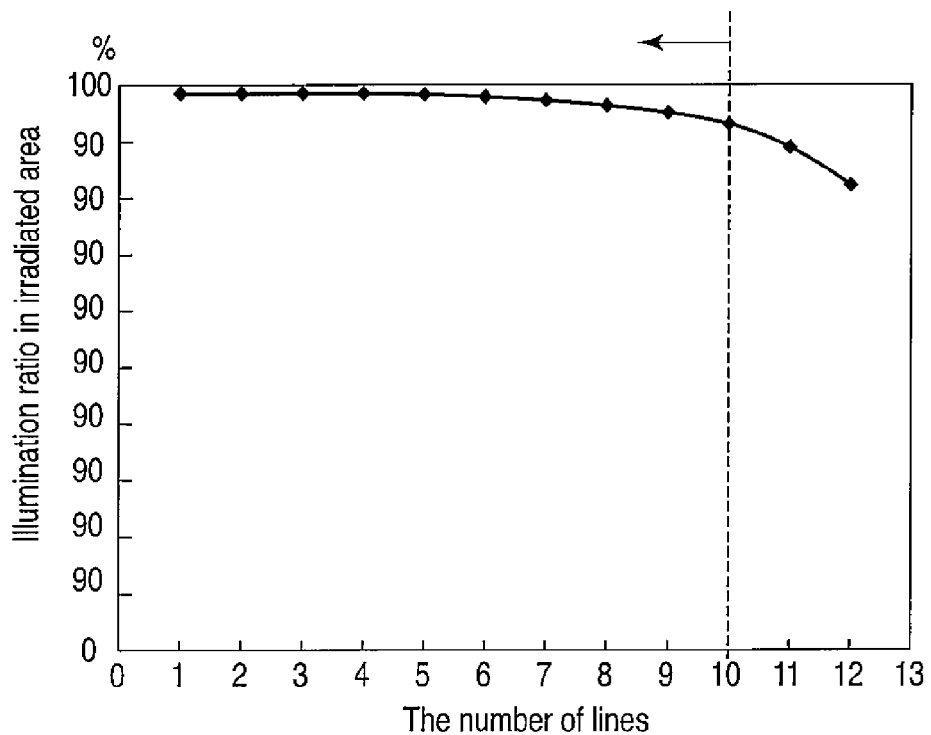
FIG. 10 is a diagram for explaining a relation between the reflection member and the illumination according to the embodiment.

The illumination ratio is calculated, based on the fluctuation quantity (for example, the absolute value of the maximum fluctuation quantity) of the illumination in the irradiation range and the illumination in the standard position (z=0). In addition, the illumination ratio is obtained by simulation for each number of lines of the reflection member 11. As a result of simulation, FIG. 10 illustrates a relation between the illumination ratio and the number n of lines of the reflection member 11. As illustrated in FIG. 10, it can be determined that fluctuations in the illumination are less than 10% when the illumination ratio is 90% or more.

Specifically, as illustrated in FIG. 10, when the number n of lines of the reflection member 11 is 10 or less, it is possible to maintain the illumination ratio at 90% or more. In other words, when the number of lines of the mirror of the reflection member 11 does not exceed 10, the illumination apparatus 10 can apply light of a proper illumination distribution to the irradiation range.

Installing the light-emitting devices 12 and the reflection member 11 as described above enables light of the light-emitting devices 12 to converge on the reading range of the reading module 6.

Specifically, according to the illumination apparatus 10 of the present embodiment, mirror images of the light-emitting devices 12 reflected on the respective mirror surfaces of the lines of the reflection member 11 illuminate the reading range of the reading module 6. According to this structure, the illumination apparatus 10 can realize an irradiation range which has uniform illumination in the carrying direction of the sheets 7 (that is, the shorter axis direction of the illumination apparatus 10). Consequently, it is possible to realize illumination apparatus 10 which has a wide margin for attachment error and manufacturing error of the illumination apparatus 10 and the reading module 6. Specifically, according to the present embodiment, it is possible to provide an illumination apparatus which can realize high illumination and high illumination uniformity, and an image reading apparatus including the illumination apparatus.

Figure 11:
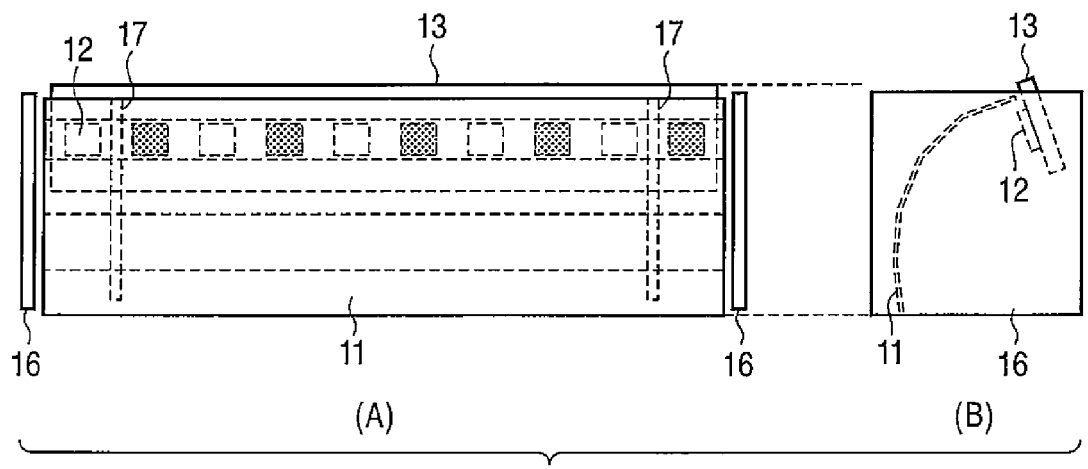
FIG. 11A is a diagram for explaining another structure example of the reflection member according to the embodiment.
FIG. 11B is a diagram for explaining another structure example of the reflection member according to the embodiment.

The illumination apparatus 10 may further include edge mirrors 16 as illustrated in FIG. 11, to enhance illumination uniformity in a direction perpendicular to the carrying direction of the sheet 7 (that is, the longitudinal direction of the light source 15).

Reference symbol A of FIG. 11 denotes the illumination apparatus 10 as viewed from the carrying direction of the sheet 7. Reference symbol B of FIG. 11 illustrates the illumination apparatus 10 as viewed from a direction perpendicular to the carrying direction of the sheet 7. As illustrated in FIG. 11, each edge mirror 16 is a mirror which has a plane shape and a mirror surface (reflection surface). The edge mirrors 16 are provided at ends in the longitudinal direction of the illumination apparatus 10, to hold the reflection member 11 and the light source module 15 therebetween. For example, the edge mirrors 16 are provided to have a mirror surface which is parallel with the surface formed by the x axis and the z axis illustrated in FIG. 7.

FIG. 12 illustrates a simulation results of an illumination distribution in the illumination apparatus 10 having the edge mirrors 16. FIG. 12 is a graph which is standardized such that the maximum value of the illumination is 1. When no edge mirrors 16 are provided, the illumination decreases in end parts of the illumination apparatus 10. However, when the edge mirrors 16 are provided, the illumination apparatus 10 can illuminate the irradiation range with light which has high illumination uniformity in the longitudinal direction, as illustrated in FIG. 12.

Second Embodiment

Although it is explained in the above embodiment that the illumination apparatus 10 has the structure of including one reflection member 11 and one light source module 15, the illumination apparatus 10 is not limited to this structure. As illustrated in FIG. 13, the illumination apparatus 10 may have a structure of including two reflection member 11 and two light source modules 15.

FIG. 13 illustrates another structure example of the image reading apparatus 117. The illumination apparatus 10 further includes a reflection member 21 and a light source module 25. The reflection member 21 has the same structure as the reflection member 11. The light source module 25 has the same structure as the light source module 15. Specifically, the light source module 25 includes light-emitting devices 22, a mounting board 23, and a heat radiation member 24.

The reflection member 21 and the reflection member 11 are symmetrical, and the light source module 25 and the light source module 15 are symmetrical, with respect to an imaging optical axis of a reading module 6. Specifically, a mirror of the reflection member 21 is formed in a bent line shape along a second standard oval which has a major axis being a straight line that has an angle −θ with the imaging optical axis of the reading module 6. A first standard oval which serves as the standard of the reflection member 11 and the second standard oval are symmetrical with respect to the imaging optical axis of the reading module 6.

The mirror of the reflection member 21 has a shape formed of a plurality of straight lines which are inscribed or circumscribed with an arc of the second standard oval. The mirror of the reflection member 21 may have a shape in which joints of the bent line of the mirror are located on or in the vicinity of the second standard oval. The shape of the mirror of the reflection member 21 can be specified by the same method as that of the mirror of the reflection member 11, and thus detailed explanation thereof is omitted.

Figure 14:
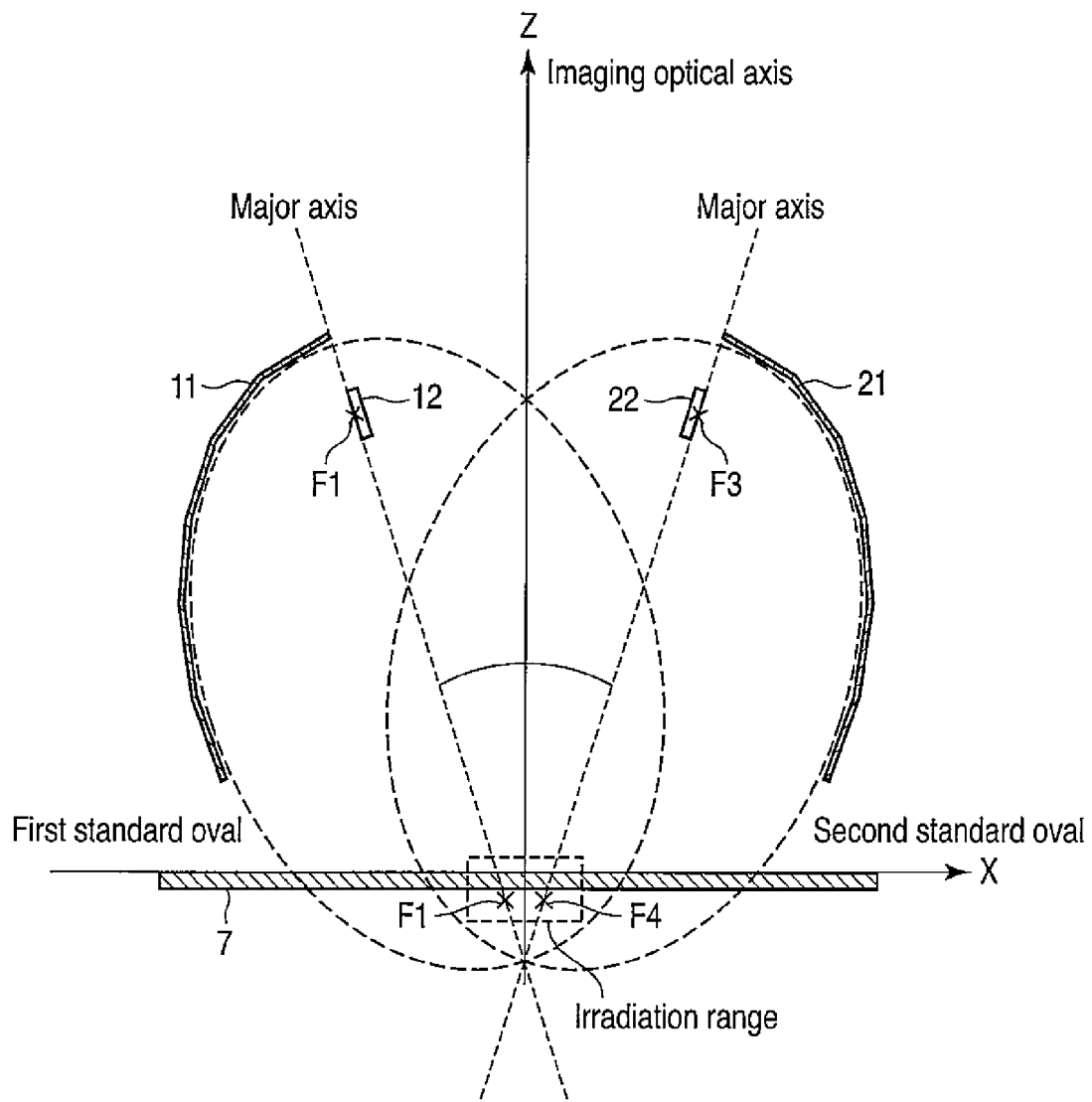
FIG. 14 is a diagram for explaining another example of the arranging position of the illumination apparatus according to the embodiment.

The reflection member 21 and the light-emitting devices 22 of the light source module 25 are arranged in, for example, positions illustrated in FIG. 14. For example, the light-emitting devices 22 are arranged in a position of a focus F3 of the second standard oval which serves as the standard of the reflection member 21. The reflection member 21 is provided such that another focus F4 of the second standard oval is located in the vicinity of the reading range of the reading module 6.

The irradiation range on the surface of sheet 7 irradiated by the light source module 15 is preferably located in a position close to the light-emitting devices 22 provided closer to a focus F1 than a focus F2. The reflection member 11 is formed based on the standard oval (first standard oval) in which the irradiation range on the sheet 7 is located in a position closer to the focus F1 than the focus F2. In this case, the focus F2 is located on a side opposite to the focus F1, with the carrying path 115 interposed therebetween.

In addition, the irradiation range on the surface of the sheet 7 irradiated by the light source module 25 is preferably located in a position close to the light-emitting devices 22 which is closer to the focus F3 than the focus F4. The reflection member 21 is formed based on the standard oval (second standard oval) in which the irradiation range on the sheet 7 is located in a position closer to the focus F3 than the focus F4. In this case, the focus F4 is located on a side opposite to the focus F3, with the carrying path 115 interposed therebetween.

Figure 15:
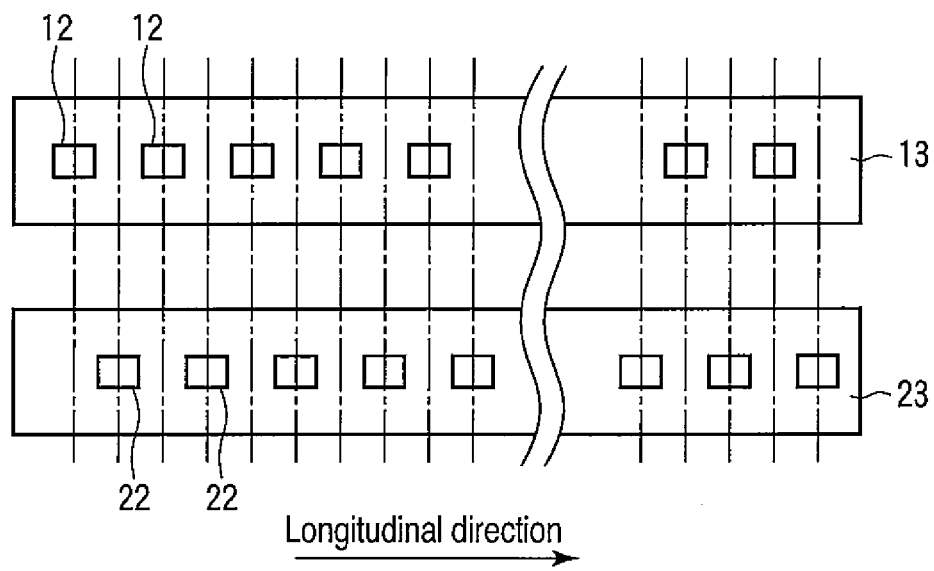
FIG. 15 is a diagram for explaining another structure example of the light source module according to the embodiment.

The light-emitting devices 12 and 22 are arranged, for example, as illustrated in FIG. 15. The light-emitting devices 12 and 22 are arranged on the mounting boards 13 and 23, respectively, such that they alternate with each other in the longitudinal direction of the illumination apparatus 10. The illumination apparatus 10 including the light-emitting devices 12 and 22 provided as described above can have increased illumination uniformity in the irradiation range.

The light-emitting devices 12 and the light-emitting devices 22 may include at least two types of light-emitting devices which emit light beams of different wavelengths. In such a case, the light-emitting devices 12 include, for example, light-emitting devices 12A which emit light of a first wavelength, and light-emitting devices 12B which emit light of a second wavelength. In addition, the light-emitting devices 22 include, for example, light-emitting devices 22A which emit light of the first wavelength, and light-emitting devices 22B which emit light of the second wavelength.

Figure 16:
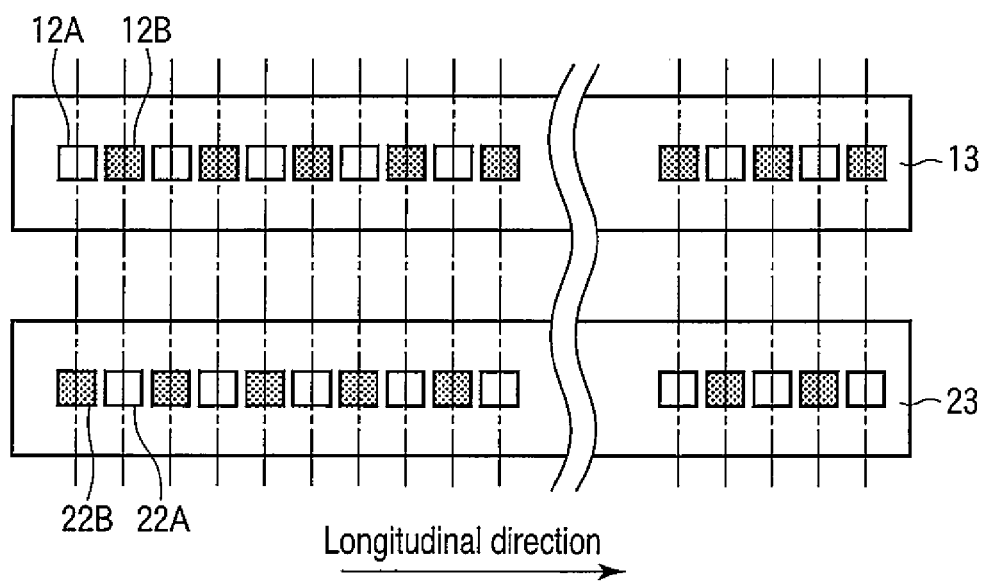
FIG. 16 is a diagram for explaining another structure example of the light source module according to the embodiment.

For example, the light-emitting devices 12A, 12B, 22A, and 22B are arranged as illustrated in FIG. 16. Specifically, the light-emitting devices 12A and 22A which emit light of the first wavelength and the light-emitting devices 12B and 22B which emit light of the second wavelength are alternately arranged on the mounting boards 13 and 23, respectively, in the longitudinal direction of the illumination apparatus 10. The illumination apparatus 10 including the light-emitting devices 12 and 22 arranged as described above can reduce unevenness in wavelength in the irradiation range.

FIG. 17 illustrates illumination distributions in the illumination apparatus 10.

A solid line in FIG. 17 indicates relation between the illumination and the number of lines in the case where the sheet 7 is not shifted in the direction of the imaging optical axis of the reading module 6. A long dashed short dashed line in FIG. 17 indicates relation between the illumination and the number of lines in the case where the sheet 7 is shifted by +1.5 mm in the direction of the imaging optical axis of the reading module 6. A dotted line in FIG. 17 indicates relation between the illumination and the number of lines in the case where the sheet 7 is shifted by −1.5 mm in the direction of the imaging optical axis of the reading module 6.

As illustrated in FIG. 17, the illumination apparatus 10 as illustrated in FIGS. 4 and 13 can apply light of high illumination uniformity in the shorter axis direction of the irradiation range, that is, in the carrying direction of the sheet 7. Consequently, it is possible to realize the illumination apparatus 10 which has a wide margin for shift of the reading range of the reading module 6 in the carrying direction of the sheet 7.

In addition, as illustrated in FIG. 17, a difference among the solid line, the dotted line, and the long dashed short dashed line is small. Specifically, the illumination apparatus 10 has a stable illumination distribution, regardless of shift of the sheet 7 in the direction of the imaging optical axis of the reading module 6. As a result, it is possible to realize the illumination apparatus 10 which has a wide margin for shift of the sheet 7 in the direction of the imaging optical axis of the reading module 6.

Specifically, the illumination apparatus 10 according to the present embodiment can realize high illumination and high illumination uniformity.

The illumination distributions obtained by the illumination apparatus 10 illustrated in FIG. 4 are asymmetrical with respect to the position of "x=0", as illustrated in FIG. 9. Therefore, there are cases where the reflection member 11 is installed such that the peak (maximum value) of the illumination distribution does not exist within the irradiation range, in view of shift of the sheet 7 in the z axis direction. In such a case, the illumination distribution in the irradiation range may change, due to error in attachment of the illumination apparatus 10.

However, as described above, the reflection member 11, the light source module 15, the reflection member 21, and the light source module 25 are provided symmetrically with respect to the position of "X=0", and thereby the illumination apparatus 10 can realize the illumination distributions as illustrated in FIG. 17. Specifically, the illumination apparatus 10 can realize an illumination distribution which is symmetrical with respect to the imaging optical axis of the reading module 6. This prevents change in illumination distribution in the irradiation range due to attachment error of the illumination apparatus 10.

In addition, as illustrated in FIG. 17, the illumination apparatus 10 can keep change in illumination for shift of the sheet 7 by ±1.5 mm in the z axis direction less than 10%.

As described above, the illumination apparatus 10 has reflection members and light source modules which are provided symmetrically with respect to the imaging optical axis of the reading module 6, and thereby can realize a symmetrical illumination distribution with respect to the imaging optical axis of the reading module 6. In addition, the illumination apparatus 10 can reduce change in illumination caused by shift of the sheet 7 in the z axis direction.

The image reading apparatus 117 which includes the illumination apparatus 10 and the reading module 6 can stably obtain images from sheets 7 which are carried at high speed. Specifically, the image reading apparatus 117 can obtain images which have small change in brightness and less unevenness of brightness, from sheets 7 which are carried at high speed.

Although the image reading apparatus 117 in the above embodiment has a structure of applying light to each of carried sheets 7 and reading an image from the sheet 7, the image reading apparatus 117 is not limited to this structure. The image reading apparatus 117 may have a structure of obtaining an image from each sheet 7 which is at a standstill, while moving the illumination apparatus 10 and the reading module 6. In such a case, the illumination apparatus 10 and the reading module 6 move together.

Although the reading module 6 in the above embodiment has the structure of obtaining reflection light of light emitted from the illumination apparatus 10, the reading module 6 is not limited to this structure. The reading module 6 may have a structure of obtaining transmission light of light emitted from the illumination apparatus 10. In such a case, the reading module 6 is provided on a side opposite to the illumination apparatus 10, with the carrying path 115 interposed therebetween. Specifically, the reading module 6 receives light which is emitted from the illumination apparatus 10 and transmitted through each sheet 7, and obtains an image.

Third Embodiment

Although it has been explained that the illumination apparatus 10 may include edge mirrors 16 as illustrated in FIG. 11 to enhance illumination uniformity in the direction perpendicular to the carrying direction of the sheets 7, the illumination apparatus 10 may further include another mirror. For example, in the case where the light-emitting devices 12 are light-emitting devices which emit light of the same wavelength, the illumination apparatus 10 may further include a double-sided mirror 17 double-sided mirror 17 inside the two edge mirrors 16.

An illumination apparatus 10 according to a third embodiment includes a board, light-emitting devices, plane mirrors (edge mirrors), and a double-sided mirror 17. The board has the same structure as that of the mounting board 13 illustrated in FIG. 11. The plane mirror has the same structure as that of the edge mirrors 16 illustrated in FIG. 11.

The board 13 can be any board, as long as light-emitting devices are fixed thereon such that the devices can apply light to a test subject and the board can supply power to the light-emitting devices.

The light-emitting devices are, for example, LEDs, and connected to the board as a light-emitting device array including the light-emitting devices arranged at regular intervals. For example, a plurality of light-emitting devices are arranged as a light-emitting device array. In addition, a plurality of light-emitting device arrays may be provided in a line.

The plane mirror is connected to the board which is located outside an end part of the light-emitting device array, such that the plane mirror is perpendicular to the arranging direction of the light-emitting devices. A plane of the plane mirror which faces the light-emitting device array is a mirror surface.

The double-sided mirror 17 is a plane mirror, both sides of which are mirror surfaces. The double-sided mirror 17 is connected to the board between light-emitting devices located at an end part of the light-emitting device array, such that the double-sided mirror 17 is perpendicular to the arranging direction of the light-emitting elements. For example, the double-sided mirror 17 is arranged between a light-emitting device, which is located outermost among the light-emitting devices of the light-emitting device array, and the second light-emitting device from the outside. The length of the double-sided mirror 17 in an irradiation direction of the light-emitting device array is set shorter than that of the plane mirror. This is because, when the length of the double-sided mirror 17 in the irradiation direction of the light-emitting devices is set longer than that of the plane mirror, the double-sided mirror 17 excessively blocks light which goes toward an end part of the light-emitting device array from light-emitting devices located around the center of the light-emitting device array, and the illumination in the end part of the array decreases.

The double-sided mirror 17 is preferably connected to the board, for example, around an intermediate point between the outermost light-emitting device and the second light-emitting device, since influence of heat radiation is uniformized. Positioning the double-sided mirror 17 around the intermediate point is preferable also for preventing structural interference between means for holding the mirror and the light-emitting devices. Actually, the double-sided mirror 17 should be connected in a proper position between the light-emitting devices, such that a difference between the maximum illumination and the minimum illumination of the light-emitting device array does not exceed threshold, in consideration of the size and a light distribution area of the light-emitting devices, and intervals at which the light-emitting devices are arranged. Although in the above example the double-sided mirror 17 is disposed between the outermost light-emitting device and the second light-emitting device from the outside, the double-sided mirror 17 may be disposed between the second light-emitting device and the third light-emitting device from the outside, as long as the difference between the maximum illumination and the minimum illumination does not exceed the threshold.

Generally, the higher effect is obtained as the size of the double-sided mirror 17 increases. However, actually, the distance between a test subject to which light is applied and the light-emitting devices is limited, and the size of the whole illumination apparatus 10 is also limited. Therefore, a proper size of the double-sided mirror 17 should be selected to fit the above conditions, such that the length is shorter than the length of the plane mirror in the irradiation direction of the light-emitting device array.

Light which is applied onto the test subject by arranging the plane mirror and the double-sided mirror 17 as described above can have some patterns. For example, among light beams emitted from the light-emitting devices, there are light which is directly applied onto the test subject, light which is reflected by the plane mirror and applied onto the test subject, light which is reflected by the double-sided mirror 17 and applied onto the test subject, and light which is reflected by the plane mirror and the double-sided mirror 17 a plurality of times and applied onto the test subject.

Without no plane mirror or double-sided mirror 17, these light beams are not applied to the test subject, or, for example, the light-emitting devices located in an end part of the light-emitting device array applies light to a part of the surface of the test subject which is located under the other end part of the light-emitting device array, and sufficient illumination cannot be obtained for a part of the surface of the test subject which is located directly under the end part. However, according to the present embodiment, the plane mirror and the double-sided mirror 17 are provided, and thereby it is possible to apply light to the part of the surface of the test subject which is located directly under the light-emitting devices of the end part of the light-emitting device array, by an effect of two mirrors that face each other, which is obtained by the plane mirror and the double-sided mirror 17. This structure prevents decrease in illumination distribution around the end part, and improves the whole illumination uniformity.

It suffices that the plane mirror and the double-sided mirror 17 are connected to one of end parts of the light-emitting device array. In the case of arranging two or more light-emitting device arrays, it suffices that the plane mirror is connected to the two or more light-emitting device arrays, and the double-sided mirror 17 is connected between the light-emitting devices, in the same manner as in the case of using one light-emitting device array. In such a case, a plurality of plane mirrors and double-sided mirror 17s may be used, such as the case where a plurality of illumination apparatuses 10, in each of which a plane mirror and a double-sided mirror 17 are connected to one light-emitting device array, are arranged, or a plane mirror and a double-sided mirror 17 may be connected to two or more light-emitting device arrays.

The effect obtained by the above structure is explained on the basis of a simulation result of the illumination distribution of the illumination apparatus 10 according to the third embodiment.

In the case of providing no plane mirror or double-sided mirror 17, the relative illumination gradually decreases from the center of the light-emitting device array toward the end parts of the light-emitting device array, and the relative illumination of the light-emitting device array decreases to about 0.72. The relative illumination is an illumination obtained when the maximum value is 1.

When the plane mirror and the double-sided mirror 17 are provided, the property that the relative illumination decreases around the end parts of the light-emitting device array is improved, and relative illumination of about 0.84 can be secured around the end parts.

According to the third embodiment described above, a plane mirror is provided at an end part of the light-emitting device array, and a double-sided mirror 17 is provided between light-emitting devices around an end part of the light-emitting device array such that the difference between the maximum illumination and the minimum illumination of the light-emitting device array does not exceed the threshold. Thereby, it is possible to prevent decrease in the relative illumination in the end parts of the light-emitting device array, and obtain high illumination uniformity.

Fourth Embodiment

Although an illumination apparatus according to a fourth embodiment is almost the same as the illumination apparatus 10 according to the third embodiment, they are different in arrangement of the double-sided mirror 17.

The following is explanation of the illumination apparatus according to the fourth embodiment.

The double-sided mirror 17 according to the third embodiment is disposed in just an intermediate position between two light-emitting devices. Specifically, the double-sided mirror 17 of the third embodiment is disposed on a straight line which runs through an intermediate point between the outermost light-emitting device and the second light-emitting device. On the other hand, a double-sided mirror 17 according to a fourth embodiment is disposed closer to the outermost light-emitting device, and shifted from a straight line which runs through an intermediate point between the outermost light-emitting device and the second light-emitting device.

By adopting the above structure, it is possible to collect light, which is emitted from light-emitting devices located around end parts of the light-emitting device array and goes toward the center of the test subject, onto end parts of the surface of the test subject more than the third embodiment, and increase the whole illumination uniformity. In addition, the illumination uniformity can be increased more, also in the case where the illumination apparatus is used in combination with light-collecting means such as a cylindrical lens provided along the light-emitting device array, and a reflection mirror, and irradiated light beams are narrowed down in use.

The above effect is explained based on a simulation result of the illumination distribution of the illumination apparatus according to the fourth embodiment.

According to the simulation result, a relative illumination around end parts of the light-emitting device array is about 0.90, which is higher than the relative illumination around end parts of the light-emitting device array of the illumination apparatus 10 according to the third embodiment. In addition, a relative illumination of the whole light-emitting device array is also 0.90 or more, and thus high illumination uniformity can be secured.

According to the fourth embodiment described above, the double-sided mirror 17 is disposed closer to the outermost light-emitting device in an end part of the light-emitting device array and shifted from an intermediate point between two light-emitting devices, and thereby illumination uniformity is further improved.

Fifth Embodiment

A fifth embodiment is different from the third embodiment and the fourth embodiment, in that a plane mirror and a double-sided mirror 17 are provided in each of end parts of an illumination apparatus.

For example, the illumination apparatus may have a structure in which a plane mirror and a double-sided mirror 17 are provided on each of both ends, by using the method of arranging the plane mirror and the double-sided mirror 17 according to the third embodiment. The illumination apparatus may have a structure in which a plane mirror and a double-sided mirror 17 are provided on each of both ends, by using the method of arranging the plane mirror and the double-sided mirror 17 according to the fourth embodiment. The arranging method according to the third embodiment may be used for one end part of the illumination apparatus, and the arranging method according to the fourth embodiment may be used for the other end part of the illumination apparatus.

The following is explanation of simulation results of an illumination distribution of the illumination apparatus according to the fifth embodiment.

According to a simulation result in the case where plane mirrors and double-sided mirror 17s are not provided in end parts of the illumination apparatus, the relative illumination in both end parts of the illumination apparatus comparatively decreases in comparison with the relative illumination around the center of the light-emitting device array.

According to a simulation result in the case where the method of arranging the plane mirror and the double-sided mirror 17 of the third embodiment is adopted for both end parts of the illumination apparatus, decrease in the relative illumination of both end parts of the light-emitting device array is improved, and a relative illumination of about 0.84 can be secured around the end parts.

According to a simulation result in the case where the method of arranging the plane mirror and the double-sided mirror 17 of the fourth embodiment is adopted for both end parts of the illumination apparatus, a relative illumination of about 0.90 can be secured around the end parts.

According to the fifth embodiment described above, the plane mirror and the double-sided mirror 17 according to the third and the fourth embodiment are arranged at each of both ends of the illumination apparatus, and thereby the illumination uniformity of the whole illumination apparatus can be improved.

Functions described in the above embodiment may be constituted not only with use of hardware but also with use of software, for example, by making a computer read a program which describes the functions. Alternatively, the functions each may be constituted by appropriately selecting either software or hardware.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

EXPLANATION OF REFERENCE SYMBOLS

6 . . . Reading module, 7 . . . Sheets, 10 . . . Illumination apparatus, 11 . . . Reflection member, 12 . . . Light-emitting device, 13 . . . Mounting board, 14 . . . Heat radiation member, 15 . . . Light source module, 16 . . . Edge mirror, 21 . . . Reflection member, 22 . . . Light-emitting device, 23 . . . Mounting board, 24 . . . Heat radiation member, 25 . . . Light source module, 100 . . . Sheet processing apparatus, 112 . . . Inlet module, 113 . . . Takeout module, 114 . . . Adsorption roller, 115 . . . Carrying path, 116 . . . Check module, 117 . . . Image reading apparatus, 119 . . . Thickness checking module, 151 . . . Main controller, 151a . . . Storage module, 152 . . . Carrying controller, 153 . . . Accumulation and binding module, 154 . . . Other sensors, 155 . . . CPU, 156 . . . Cutting controller.

What is claimed is:

1. An illumination apparatus for an image reading apparatus which receives light from a reading range and acquires an image, the illumination apparatus comprising:
   a first light source module which includes a light-emitting module that emits light, the light-emitting module having a line shape; and
   a first reflection member which includes a first reflection surface that reflects the light emitted from the light-emitting module of the first light source module for the reading range,
   wherein the first reflection surface has a cross section that has a zigzag line shape including a plurality of line segments running along a standard oval, which has a major axis that forms a predetermined angle with a direction perpendicular to the reading range, in a direction perpendicular to a longitudinal direction of the light-emitting module of the first light source module,
   the light-emitting module of the first light source module is disposed in a position of a first focus of the standard oval,
   the first reflection member is disposed so that the reading range arranged within limits beforehand set up on an imaging optical axis of the image reading apparatus from a second focus of the standard oval, and
   the cross-sectional zigzag line shape is formed by tangents of the respective intersection points of the standard oval and lines drawn from the second focus of the standard oval at equal angles to the standard oval.

2. The illumination apparatus according to claim 1, wherein
   the first reflection member is disposed, such that a second focus of the standard oval is disposed in a position opposed to the first focus with the reading range interposed therebetween.

3. The illumination apparatus according to claim 2, wherein
   the number of the line segments of the zigzag shape of the first reflection surface is determined based on fluctuations in illumination in the reading range for shift of a test subject in the direction perpendicular to the reading range.

4. The illumination apparatus according to claim 1, wherein the first light source module includes a light source module in which a plurality of light-emitting devices that emit light are arranged in a line.

5. The illumination apparatus according to claim 4, further comprising:
   a plane mirror which is disposed in at least one of end parts of the light-emitting module and perpendicularly to an arranging direction of the light-emitting devices; and
   a double-sided mirror which is disposed between two adjacent light-emitting devices among the light-emitting devices and perpendicularly to the arranging direction of the light-emitting devices, such that a difference between a maximum illumination of the light-emitting module and a minimum illumination of the light-emitting module does not exceed a threshold,
   the double-sided mirror has a length which is smaller than a length of the plane mirror, in an irradiation direction of the light-emitting module.

6. The illumination apparatus according to claim 5, wherein
the double-sided mirror is disposed closer to an end part of the light-emitting module and shifted from an intermediate point between the two adjacent light-emitting modules.

7. The illumination apparatus according to claim 5, wherein
the double-sided mirror is disposed between a first light-emitting device, which is located outermost among the light-emitting devices in the arranging direction, and a second light-emitting device which is located in a second position from outside, or between the second light-emitting device and a third light-emitting device which is located in a third position from outside.

8. The illumination apparatus according to claim 5, wherein
the plane mirror is disposed in both end parts of the light-emitting module and perpendicularly to the arranging direction of the light-emitting devices, and
the double-sided mirror is disposed between a light-emitting device disposed in each end part of the light-emitting module and a light-emitting module which is adjacent to the light-emitting element and closer to a center of the light-emitting module.

9. The illumination apparatus according to claim 5, wherein
the first light source module further includes another or more light-emitting module provided in a line with the light-emitting module, and the plane mirror and the double-sided mirror are disposed on a plane, which is perpendicular to a plane formed by the light-emitting modules and to which the light emitted by the light-emitting devices is emitted.

10. The illumination apparatus according to claim 4, wherein
the light-emitting module includes a plurality of light-emitting devices which emit light of a first wavelength, and a plurality of light-emitting devices which emit light of a second wavelength, and
the light-emitted devices which emit light of the first wavelength are alternated with the light-emitting devices which emit light of the second wavelength in a line.

11. The illumination apparatus according to claim 1, wherein
the first reflection member further includes reflection surfaces which reflect light and are provided to hold the first reflection surface and the light-emitting module of the first light source module therebetween, in the longitudinal direction of the light-emitting module of the first light source module.

12. The illumination apparatus according to claim 1, further comprising:
a second light source module which has a light-emitting module that emits light, the light-emitting module having a line shape; and
a second reflection member which has a second reflection surface that reflects the light emitted from the light-emitting module of the second light source module for the reading range,
wherein the light-emitting module of the second light source module is provided in a position symmetrical with the light-source module of the first light source module, with respect to a plane which includes the direction perpendicular to the reading range and the longitudinal direction and the longitudinal direction of the light source module of the first light source module, and the second reflection surface is provided in a position symmetrical with the first reflection surface, with respect to the plane which includes the direction perpendicular to the reading range and the longitudinal direction and the longitudinal direction of the light source module of the first light source module.

13. The illumination apparatus according to claim 12, wherein
each of the first and the second light source modules includes a light-emitting module in which a plurality of light-emitting devices which emit light are arranged in a line at predetermined intervals, and
the light-emitting devices of the first and the second light source modules are alternated in the longitudinal direction of the light-emitting modules of the first and the second light source modules.

14. The illumination apparatus according to claim 12, wherein
the first light source module includes a light-emitting module in which a plurality of light-emitting devices which emit light of a first wavelength are alternated with a plurality of light-emitting devices which emit light of a second wavelength in a line, and
the second light source module includes a light-emitting module in which a plurality of light-emitting devices which emit light of the first wavelength are alternated with the plurality of light-emitting devices which emit light of a second wavelength in a line in a order reverse to that of the light-emitting devices of the light-emitting module of the first light source module.

15. An image reading apparatus which receives light from a reading range and acquires an image, the image reading apparatus comprising:
a light source module which includes a light-emitting module that emits light, the light-emitting module having a line shape;
a reflection member which includes a reflection surface that reflects the light emitted from the light-emitting module of the light source module for a reading range; and
a reading module which receives light from the reading range, and obtains an image,
wherein the reflection surface has a cross section that has a zigzag line shape including a plurality of line segments running along a standard oval, which has a major axis that forms a predetermined angle with a direction perpendicular to the reading range, in a direction perpendicular to a longitudinal direction of the light-emitting module of the light source module,
the light-emitting module of the light source module is disposed in a position of a first focus of the standard oval,
the reflection member is disposed so that the reading range arranged within limits beforehand set up on an imaging optical axis of the image reading apparatus from a second focus of the standard oval, and
the cross-sectional zigzag line shape is formed by tangents of the respective intersection points of the standard oval and lines drawn from the second focus of the standard oval at equal angles to the standard oval.

16. An illumination apparatus for image reading apparatus which receives light from a reading range, and acquires an image, the illumination apparatus comprising:
a first light source module which includes a light-emitting module that emits light, the light-emitting module having a line shape; and a first reflection member which includes a first reflection surface that reflects the light emitted from the light-emitting module of the first light source module for the reading range, wherein the first reflection surface has a cross section that has a zigzag line shape including a plurality of line segments running along a standard oval, which has a major axis that forms a predetermined angle with a direction perpendicular to the reading range, in a direction perpendicular to a longitudinal direction of the light-emitting module of the first light source module, the light-emitting module of the first light source module is disposed in a position of a first focus of the standard oval, the first reflection member is disposed so that the reading range arranged within limits beforehand set up on an imaging optical axis of the image reading apparatus from a second focus of the standard oval, the cross-sectional zigzag line shape is formed with intersection points as bent points between the tangents of the respective intersection points of the standard oval and lines drawn from the second focus of the standard oval at the equal angle to the standard oval.

17. The illumination apparatus according to claim 16, wherein the first reflection member is disposed, such that a second focus of the standard oval is disposed in a position opposed to the first focus with the reading range interposed therebetween, and the number of the line segments of the zigzag shape of the first reflection surface is determined based on fluctuations in illumination in the reading range for shift of a test subject in the direction perpendicular to the reading range.

18. The illumination apparatus according to claim 16, wherein the first light source module includes;

a light source module in which a plurality of light-emitting devices that emit light are arranged in a line;

a plane mirror which is disposed in at least one of end parts of the light-emitting module and perpendicularly to an arranging direction of the light-emitting devices; and a double-sided mirror which is disposed between two adjacent light-emitting devices among the light-emitting devices and perpendicularly to the arranging direction of the light-emitting devices, such that a difference between a maximum illumination of the light-emitting module and a minimum illumination of the light-emitting module does not exceed a threshold, the double-sided mirror has a length which is smaller than a length of the plane mirror, in an irradiation direction of the light-emitting module.

19. The illumination apparatus according to claim 16, wherein the plane mirror is disposed in both end parts of the light-emitting module and perpendicularly to the arranging direction of the light-emitting devices, and the double-sided mirror is disposed between a light-emitting device disposed in each end part of the light-emitting module and a light-emitting module which is adjacent to the light-emitting element and closer to a center of the light-emitting module.

* * * * *